United States Patent [19]

Nagase et al.

[11] Patent Number: 5,329,034

[45] Date of Patent: Jul. 12, 1994

[54] SILANOL COMPOUNDS, POLYMERIZABLE MONOMERS AND POLYMERS HAVING MESOGENIC GROUPS

[75] Inventors: Yu Nagase; Yuriko Takamura, both of Sagamihara, Japan

[73] Assignee: Sagami Chemical Research Center, Tokyo, Japan

[21] Appl. No.: 28,621

[22] Filed: Mar. 8, 1993

Related U.S. Application Data

[62] Division of Ser. No. 736,624, Jul. 26, 1991, abandoned.

[30] Foreign Application Priority Data

Aug. 9, 1990 [JP] Japan ................. 2-209325
Aug. 9, 1990 [JP] Japan ................. 2-209326
Mar. 13, 1991 [JP] Japan ................. 3-072050
Mar. 13, 1991 [JP] Japan ................. 3-072051

[51] Int. Cl.$^5$ .............. C07F 7/08; C07F 7/10; C07F 7/18
[52] U.S. Cl. .................. 556/415; 556/418; 556/440; 534/566; 534/577; 552/505
[58] Field of Search .......... 556/415, 440, 418; 534/566, 577; 552/505

[56] References Cited

U.S. PATENT DOCUMENTS

| | | | |
|---|---|---|---|
| 4,358,391 | 11/1982 | Finkelmann et al. | 556/440 UX |
| 4,824,950 | 4/1989 | Barcza | 556/440 X |
| 4,910,232 | 3/1990 | Arai | 556/440 X |
| 4,916,247 | 4/1990 | Steinmann | 556/440 X |
| 5,113,004 | 5/1992 | Yanagisawa et al. | 446/550 |

OTHER PUBLICATIONS

Pure & Appl. Chem., vol. 57, No. 7, pp. 1009–1014, 1985, M. Engel, et al., "Synthesis, Structure and Properties of Liquid Crystalline Polymers".

*Primary Examiner*—Paul F. Shaver
*Attorney, Agent, or Firm*—Oblon, Spivak, McClelland, Maier & Neustadt

[57] ABSTRACT

A silanol compound having a mesogenic group, of the following formula (III):

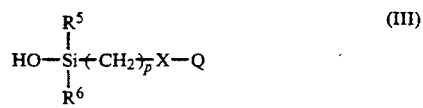

wherein each of $R^5$ and $R^6$, which may be the same or different, is an alkyl group or a phenyl group, X is a single bond, an oxygen atom, or a group of the formula —COO— or "OCO—, Q is a mesogenic group, and p is an integer of from 2 to 20, and a process for its production. Also disclosed are a polymerizable monomer of the following formula (I) and a polymer having repeating units of the following formula (II).

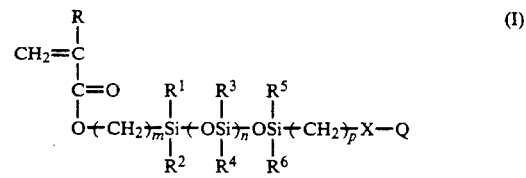

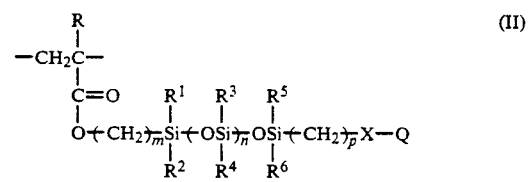

wherein R is a hydrogen atom, a halogen atom, an alkyl group or a phenyl group, each of $R^1$ to $R^6$ which may be the same or different, is an alkyl group or a phenyl group, m is an integer of from 2 to 20, n is an integer of from 0 to 50, and X, Q and p are as defined above.

7 Claims, No Drawings

SILANOL COMPOUNDS, POLYMERIZABLE MONOMERS AND POLYMERS HAVING MESOGENIC GROUPS

This application is a division of U.S. patent application Ser. No. 07/736,624, filed on Jul. 26, 1991, now abandoned.

The present invention relates to novel silanol compounds having mesogenic groups and a process for their production. The silanol compounds of the present invention are novel liquid crystal compounds, and they are particularly useful as intermediates for the synthesis of monomers which are useful for the synthesis of novel side chain liquid crystalline polymers having siloxane bonds as spacers. Thus, the present invention relates also to novel polymerizable monomers having mesogenic groups, wherein a polymerizable group and a mesogenic group are bonded by means of a spacer containing a siloxane bond, and novel polymers having mesogenic groups, obtainable by polymerization of such monomers, wherein a backbone structure and a mesogenic group are bonded by means of a spacer containing a siloxane bond. The polymers having mesogenic groups of the present invention are particularly useful as side chain liquid crystalline polymers showing stable liquid crystalline phase at a relatively low temperature i.e. at room temperature or a lower temperature.

Heretofore, side chain liquid crystalline polymers having mesogenic groups on side chains have been studied for a wide range of applications as functional materials for display elements or recording materials in the electronics field or recently as functional materials useful for non-linear optical materials or light-controlling glass. Conventional side chain liquid crystalline polymers have a structure in which mesogenic groups are bonded to the polymer backbone by means of a chemical bond called a spacer. As the backbone structure, polymers such as polymethacrylate, polyacrylate, polyether, polyorganosiloxane and polyester are known, and many side chain liquid crystalline polymers have been proposed. (For example, Liquid Crystal Polymer, CMC, compiled by Naoyuki Koide (1987); R. Zentel, "Liquid Crystalline Polymers", Kem. Ind., vol 37, p. 355 (1988); V. P. Shibaev, "Synthesis and Structure of Liquid-crystalline Side-chain Polymers", Pure & Appln. Chem. vol 57, p. 1589 (1985); T. Chung, "The Recent Developments of Thermotropic Liquid Crystalline Polymers", Polym. Eng. Sci., vol 26, p. 901 (1986).)

Further, it has been reported that by means of a spacer, the mobility of the backbone structure and that of the mesogenic groups tend to be independent, whereby orientation of liquid crystals will be facilitated, and by means of a longer spacer for higher mobility, a more stable liquid crystalline phase can be obtained (Naoyuki Koide, "Synthesis of Polymer Liquid Crystals", Kobunshi, vol 36, p. 98 (1987)). Heretofore, most of chemical bonds known as such spacers are alkylene groups or oxyalkylene groups.

However, when such spacers are used for the above mentioned backbone structures, the temperatures at which polymers show liquid crystalline phase are usually high, and in most cases, they show no liquid crystalline phase at temperatures around room temperature.

In view of such a drawback of side chain liquid crystalline polymers having conventional spacers, it is an object of the present invention to provide a side chain liquid crystalline polymer which exhibits stable liquid crystalline phase at a relatively low temperature i.e. at room temperature or a lower temperature, by introducing into the spacer an alkylene group having a siloxane bond having very high mobility, and an intermediate useful for the production of such a side chain liquid crystalline polymer.

The present inventors have conducted extensive researches to synthesize a side chain liquid crystalline polymer having a siloxane bond in the spacer. As a result, they have found that a novel silanol compound having a mesogenic group can be synthesized, the obtained silanol compound exhibits liquid crystalline phase by itself, it can be used also as a starting material for the preparation of a novel monomer in which a mesogenic group and a polymerizable group are bonded by means of a siloxane bond, and such a monomer can be polymerized to obtain a side chain liquid crystalline polymer having a siloxane bond in the spacer. The present invention has been accomplished on the bases of these discoveries.

Namely, the present invention provides a silanol compound having a mesogenic group, of the following formula (III):

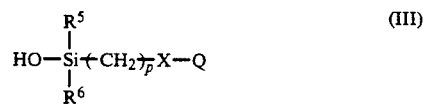

wherein each of $R^5$ and $R^6$, which may be the same or different, is an alkyl group or a phenyl group, X is a single bond, an oxygen atom, or a group of the formula —COO— or "OCO—, Q is a mesogenic group, and p is an integer of from 2 to 20.

The present invention also provides a process for producing a silanol compound of the above formula (III), which comprises reacting an alkenyl compound having a mesogenic group, of the following formula (VI):

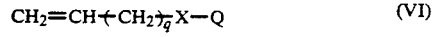

wherein X and Q are as defined above, and q is an integer of from 0 to 18, and a compound of the following formula (VII):

wherein $R^5$ and $R^6$ are as defined above, and R' is an alkyl group, in the presence of a hydrosilylation catalyst, by mixing them so that the compound of the above formula (VII) would be at least equimolar to the compound of the above formula (Vi), to obtain a compound of the following formula (VIII):

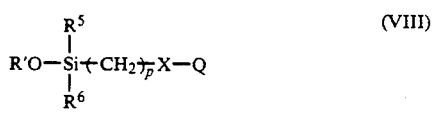

wherein $R^5$, $R^6$, $R'$, $Q$ and $p$ are as defined above, and hydrolyzing the compound of the above formula (VIII) to obtain the compound of the formula (III).

Further, the present invention provides a polymerizable monomer having a mesogenic group, of the following formula (I):

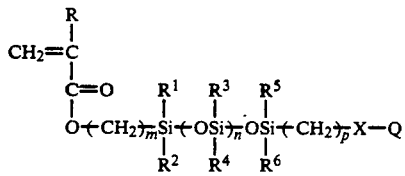

wherein R is a hydrogen atom, a halogen atom, an alkyl group or a phenyl group, each of $R^1$ to $R^6$, which may be the same or different, is an alkyl group or a phenyl group, X is a single bond, an oxygen atom, or a group of the formula —COO— or "OCO—, Q is a mesogenic group, each of m and p is an integer of from 2 to 20, and n is an integer of from 0 to 50.

Still further, the present invention provides a polymer having mesogenic groups, which has repeating units of the following formula (II):

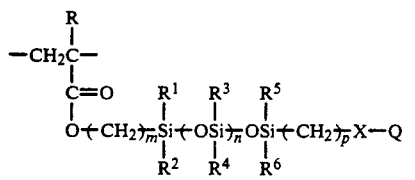

wherein R is a hydrogen atom, a halogen atom, an alkyl group or a phenyl group, each of $R^1$ to $R^6$, which may be the same or different, is an alkyl group or a phenyl group, X is a single bond, an oxygen atom, or a group of the formula —COO— or "OCO—, Q is a mesogenic group, each of m and p is an integer of from 2 to 20, and n is an integer of from 0 to 50, provided that R, $R^1$ to $R^6$, X, Q, m, n and p may be the same or different among the respective repeating units, and which has a weight average molecular weight of from 1,000 to 1,000,000 as measured, as polystyrene standards, by means of gel permeation chromatography.

Now, the present invention will be described in detail with reference to the preferred embodiments.

The mesogenic group represented by Q in the above formulas (I), (II) and (III) is a known liquid crystalline-imparting group, and there is no particular restriction as to its structure. The mesogenic group includes, for example, biphenyl, biphenyl ether, phenyl benzoate, biphenyl benzoate, benzylidene aniline, stilbene, azoxybenzene, azobenzene, a schiff base, cyclohexylphenyl ether, cyclohexylbenzene, phenyl cyclohexylcarboxylate, biphenyl cyclohexylcarboxylate, cholesterol, cholestane and derivatives thereof. Further, a polar group such as an alkyl or alkoxy group having an optically active group, a fluoroalkyl group, a cyanoalkyl group or a cyanoalkoxy group may be bonded to the above mesogen molecule, so that a special effect such as a ferroelectric nature be imparted to the silanol compound and to the polymer having mesogenic groups of the present invention.

R in the above formulas (I) and (II) may, for example, be a hydrogen atom, a halogen atom such as fluorine, chlorine, bromine or iodine, a linear or branched alkyl group such as a methyl group, an ethyl group, a propyl group, an iso-propyl group, a butyl group, a t-butyl group or a hexyl group, or a phenyl group. However, the substituent represented by this R is preferably a halogen atom or a methyl group from the viewpoint of easiness in the synthesis. The substituent for each of $R^1$ to $R^6$ in the above formulas (I) and (II) and for each of $R^5$ and $R^6$ in the above formula (III), may, for example, be a linear or branched alkyl group such as a methyl group, an ethyl group, a propyl group, an iso-propyl group, a butyl group, an iso-butyl group, a t-butyl group, a pentyl group or a hexyl group, or a phenyl group. However, a methyl group is most preferred among the above substituents, from the viewpoint of easiness in the synthesis and in order to make the best use of the characteristics of the polymer having mesogenic groups of the present invention. The methylene chain in the above formulas (I), (II) and (III) is required to have a certain length. Accordingly, the number of methylene groups represented by each of m and p in these formulas is required to be within a range of from 2 to 20. However, each of m and p is more preferably within a range of from 3 to 10 from the viewpoint of easiness in the synthesis and in order to make the best use of the characteristics of the polymer having mesogenic groups of the present invention.

The polymerizable monomer of the above formula (I) of the present invention can readily be prepared by e.g. the following synthetic routes.

Namely, a method represented by the following "route 1" can be used in a case where the degree of polymerization of the siloxane chain represented by n in the above formula (I) is 0 i.e. in a case where a monomer wherein a polymerizable group and a mesogenic group are bonded by means of a spacer containing a disiloxane bond, is to be prepared:

Route 1

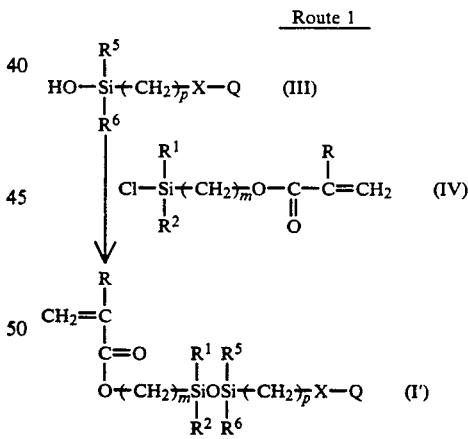

wherein R is a hydrogen atom, a halogen atom, an alkyl group or a phenyl group, each of $R^1$, $R^2$, $R^5$ and $R^6$, which may be the same or different, is an alkyl group or a phenyl group, X is a single bond, an oxygen atom, or a group of the formula —COO— or "OCO—, Q is a mesogenic group, and each of m and p is an integer of from 2 to 20.

Namely, a monomer having a mesogenic group, of the above formula (I') of the present invention can be prepared by reacting a silanol compound having a mesogenic group, of the above formula (III) with a chlorosilane compound having a polymerizable group, of the above formula (IV). When the silanol compound of the above formula (III) is reacted with the chlorosilane compound of the above formula (IV), hydrogen chloride will be generated. Therefore, the reaction is preferably conducted in the presence of an organic base such as triethylamine, N,N-dimethylaniline or pyridine so that the reaction proceeds smoothly. This reaction is preferably conducted in an organic solvent. Here, as such a solvent, tetrahydrofuran, benzene, toluene, n-hexane, chloroform, carbon tetrachloride or the like may preferably be used. Further, this reaction is preferably conducted in an atmosphere of an inert gas such as argon or nitrogen. The chlorosilane compound of the above formula (IV) to be used here, includes, for example:

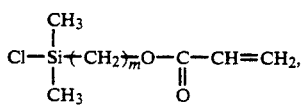

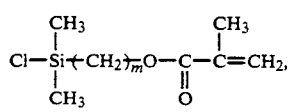

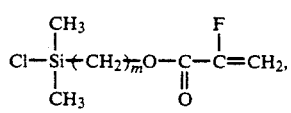

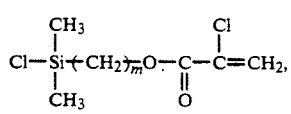

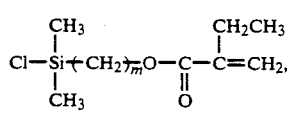

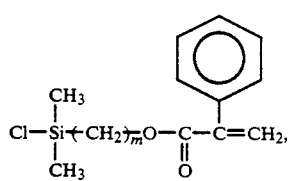

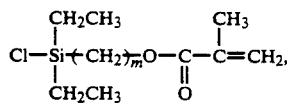

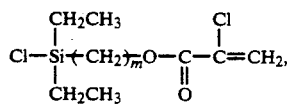

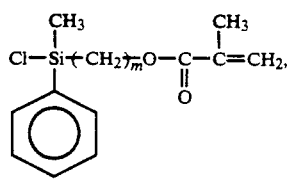

-continued

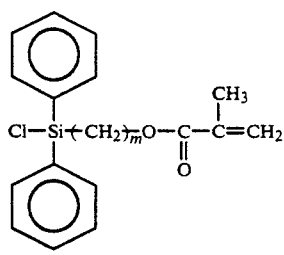

In the above formulas, m is an integer of from 2 to 20.

In a case where the polymerization degree of the siloxane chain represented by n in the above formula (i) is at least 1 i.e. in a case where a monomer in which a polymerizable group and a mesogenic group are bonded by means of a spacer containing a polysiloxane bond, is to be prepared, a method represented by the following "Route 2" can be employed:

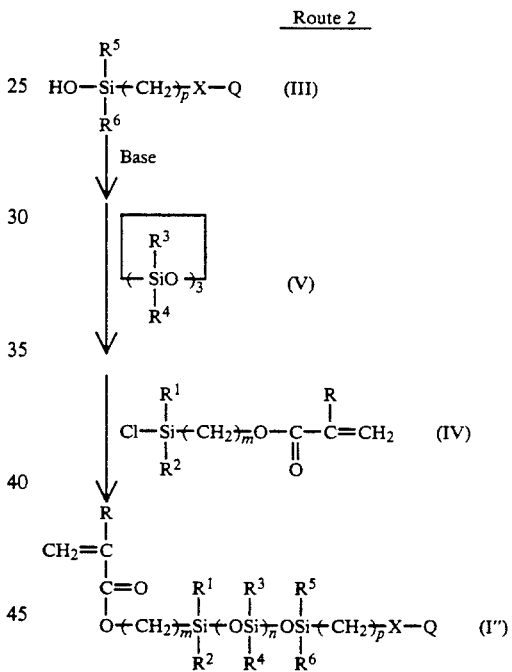

In the above formulas, R is a hydrogen atom, a halogen atom, an alkyl group or a phenyl group, each of $R^1$ to $R^6$, which may be the same or different, is an alkyl group or a phenyl group, X is a single bond, an oxygen atom, or a group of the formula —COO— or "OCO—, Q is a mesogenic group, each of m and p is an integer of from 2 to 20, and n is an integer of from 1 to 50.

Namely, a silanol compound of the above formula (III) is reacted with a base to form a silanolate anion, then living ring opening polymerization of a cyclosiloxane compound of the above formula (V) is conducted, and the reaction is terminated with a chlorosilane compound of the above formula (IV), to obtain a monomer of the above formula (I"). The base to be used here may, for example, be an organic lithium compound such as methyllithium, n-butyllithium, sec-butyllithium, t-butyllithium, phenyllithium, lithium diisopropylamide or bistrimethyllithiumamide, an alkali metal hydride such as sodium hydride or potassium hydride, or a Grignard compound such as methylmagnesium iodide, ethylmagnesium bromide or phenylmagnesium bromide. Such a base is used usually in an amount of about one equivalent to the silanol compound of the above formula (III). It is preferred to conduct the reaction at a relatively low temperature of from −90° C. to room temperature so that a side reaction can thereby be suppressed. This reaction is preferably conducted in an organic solvent. As such a solvent, tetrahydrofuran, benzene, toluene, n-hexane, chloroform, carbon tetrachloride or the like may preferably be employed. Further, this reaction is preferably conducted in an atmosphere of an inert gas such as argon or nitrogen. The cyclosiloxane compound of the above formula (V) includes, for example:

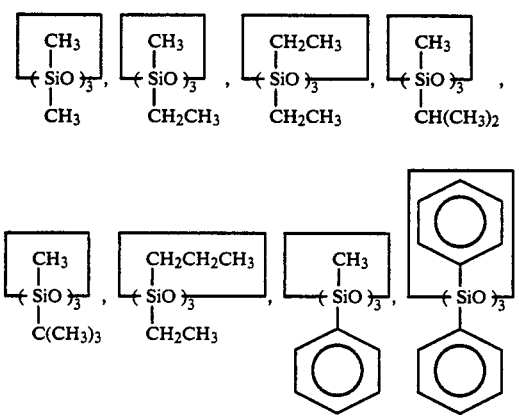

In this reaction, it is possible to control the average polymerization degree n of the polysiloxane bond in the monomer of the above formula (I″) by adjusting the amount of the cyclosiloxane of the above formula (V).

The silanot compound having a mesogenic group, of the above formula (III), which is used as a starting material in the processes for producing a polymerizable monomer having a mesogenic group, of the above formula (I) of the present invention represented by the above "Route 1" and "Route 2", may be synthesized, for example, by the following process.

Namely, an alkenyl compound having a mesogenic group, of the following formula (VI):

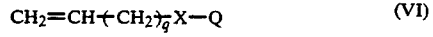

$$CH_2=CH(CH_2)_q X-Q \qquad (VI)$$

wherein X is a single bond, an oxygen atom, or a group of the formula —COO— or "OCO—, Q is a mesogenic group, and q is an integer of from 0 to 18, and an alkoxysilane compound of the following formula (VII):

wherein each of $R^5$ and $R^6$ which may be the same or different, is an alkyl group or a phenyl group, and R′ is an alkyl group, are mixed so that the compound of the above formula (VII) would be at least equimolar to the compound of the above formula (VI), and reacted in the presence of a hydrosilylation catalyst to obtain a compound of the following formula (VIII):

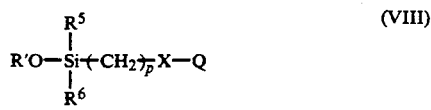

wherein $R^5$, $R^6$, R′, X, Q are as defined above, and p is an integer of from 2 to 20, and the compound of the above formula (VIII) is then hydrolized to obtain a silanol compound having a mesogenic group, of the above formula (III).

As the hydrosilylation catalyst to be used for the reaction of the alkenyl compound of the above formula (VI) and the alkoxy silane of the above formula (VII) to obtain the compound of the above formula (VIII) in the above process, it is most common to employ a platinum type catalyst such as platinum, platinum carbon, chloroplatinic acid or dicyclopentadienylplatinum dichloride. However, it is also possible to employ a metal complex containing palladium or rhodium. For example, $(Ph_3P)_4Pd$, $(Ph_3P)_2PdCl_2$, $(PhCN)_2PdCl_2$, $(Ph_3P)_3RhCl$, $(Ph_2PH)_2RhCl$, $(Ph_3P)_2(CO)RhCl$ or $[(C_2H_5)_3P]_2(CO)RhCl$ may be used as the catalyst. The catalyst may be used usually in an amount of from 1/100 to 1/1,000 equivalent relative to the alkenyl compound of the above formula (VI). To complete this reaction, it is necessary to mix the reactants so that the compound of the above formula (VII) would be at least equimolar to the compound of the above formula (VI). This reaction is preferably conducted in a solvent. As such a solvent, hexane, benzene, toluene, acetone, trichloroethylene, carbon tetrachloride, tetrahydrofuran or the like, may be employed. The reaction is conducted usually at a temperature within a range of from 40° to 100° C., and preferably conducted in an atmosphere of an inert gas such as argon or nitrogen.

The synthesis of the alkenyl compound having a mesogenic group, of the above formula (VI) can readily be accomplished by introducing an alkenyl group directly to the above mesogenic group or by introducing an alkenyl group in one of the steps for synthesizing the above mesogenic group, as will be described in Examples.

The alkoxysilane compound of the above formula (VIII) includes, for example:

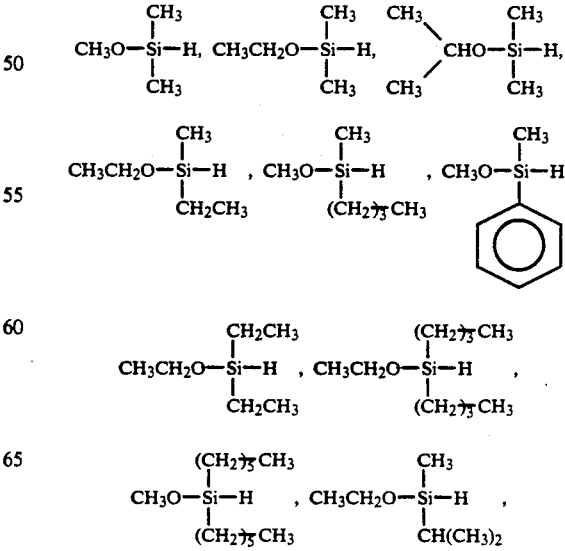

-continued

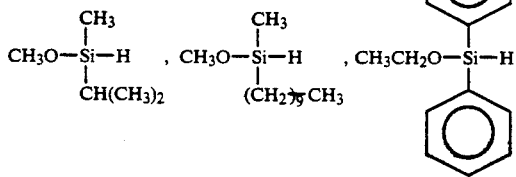

Some of them are commercially available.

The hydrolysis reaction for the preparation of the silanol compound of the above formula (III) from the compound of the above formula (VIII) is conducted usually in the presence of a base or an acid, whereby the reaction proceeds smoothly. As the base or the acid to be used, it is preferred to employ a base such as lithium hydroxide, potassium hydroxide, sodium hydroxide, aluminum hydroxide, potassium carbonate, sodium carbonate, potassium acetate or sodium acetate, or an acid such as hydrochloric acid, sulfuric acid, nitric acid, acetic acid, calcium sulfate, calcium nitrate or magnesium sulfate. When a bond susceptible to hydrolysis such as an ester bond is present in the mesogenic group Q in the above formula (VIII), it is preferred to employ a weak base or a weak acid among the above mentioned bases or acids. Such a base or an acid is used preferably within a range of from 0.1 to 5.0 equivalent to the compound of the above formula (VIII).

Further, it is necessary to conduct this reaction in the presence of water. When the compound of the above formula (VIII) is insoluble in water, an organic solvent soluble in water, such as methanol, ethanol, propanol, acetone, tetrahydrofuran or acetonitrile, may be used in combination, so that the reaction proceeds smoothly. The reaction can usually be conducted at room temperature. If the temperature is high, a disiloxane compound which is a dimmer of the desired silanol, may sometimes be formed as a byproduct. In a case where such a dimmerization reaction is likely to proceed, it is necessary to control the reaction temperature within a range of from $-100°$ C. to $0°$ C.

When a polymerizable monomer having a mesogenic group, of the above formula (I) of the present invention, obtained by the above described process, is polymerized to obtain a polymer having mesogenic groups of the present invention, wherein the repeating units are represented by the above formula (II), polymerization may be conducted by mixing two or more polymerizable monomers having mesogenic groups, of the above formula (I), and a known addition polymerization method such as radical polymerization, anionic polymerization or cationic polymerization, may be employed. However, in this case, radical polymerization is preferably employed as the simplest method. When the polymerization is conducted by the radical polymerization method, a known method such as bulk polymerization, solution polymerization or emulsion polymerization, may be employed. The radical polymerization reaction may simply be initiated by irradiation with heat or ultraviolet rays or by an addition of a radical initiator. As the radical initiator which can suitably be employed for the reaction, an organic peroxide such as dilauroyl peroxide, di-t-butyl peroxide, benzoyl peroxide, t-butyl hydroperoxide or cumene hydroperoxide, or an azo compound such as $\alpha,\alpha'$-azobisisobutyronitrile or azobiscyclohexanecarbonitrile, may be mentioned.

Further, the molecular weight of the resulting polymer can be controlled to some extent by adding a chain transfer agent during the polymerization reaction. As the chain transfer agent to be used here, carbon tetrachloride, bromotrichlorobutane p-benzoquinone, chloroanile, n-butane thiol, n-dodecane thiol or the like may be mentioned. As the organic solvent to be used for the radical polymerization reaction, it is possible to employ benzene, toluene, chlorobenzene, tetrahydrofuran, chloroform, methyl ethyl ketone, fluorobenzene, methanol, ethanol, n- or i-propanol, N,N-dimethylformamide or N,N-dimethylacetoamide. However, the solvent is not limited to such specific examples. The reaction usually proceeds smoothly within a temperature range of from $40°$ to $100°$ C.

The polymer having mesogenic groups of the present invention thus obtained, may be a copolymer having two or more kinds of repeating units. Namely, in the above formula (II), the groups represented by R, $R^1$ to $R^6$, X and Q, and m, n and p, may be optionally different among the repeating units. Further, the weight average molecular weight of this polymer is required to be from 1,000 to 1,000,000 as a value obtained as polystyrene standards by means of gel permeation chromatography. Further, in a case where a film is, for example, prepared from this polymer and its strength is important, the weight average molecular weight is preferably at least 10,000.

The polymer having mesogenic groups of the present invention wherein the repeating units are represented by the above formula (II), which can readily be prepared from a polymerizable monomer having a mesogenic group, of the above formula (I) of the present invention by the above described process, has a siloxane bond having high mobility in the spacer, whereby the glass transition temperature is low at a level of room temperature or lower, and the polymer exhibits very stable crystallizability in a wide temperature range from a relatively low temperature i.e. at a room temperature or a lower temperature, as shown in some of Examples given hereinafter. Accordingly, the polymer having mesogenic groups of the present invention is useful for display materials, recording materials or non-linear optical materials in the electronics fields and for various other applications such as light-controlling glass material or separating membrane materials in which its characteristics are advantageously utilized.

Now, the present invention will be described in further detail with reference to examples. However, it should be understood that the present invention is by no means restricted to such specific examples. In the following reaction formulas, $D_3$ represents hexamethylcyciotrisiioxane, n-BuLi represents n-butyllithium, and AIBN represents azobisisobutylonitrile.

EXAMPLE 1

Synthesis 1 of a silanol compound having a mesogenic group

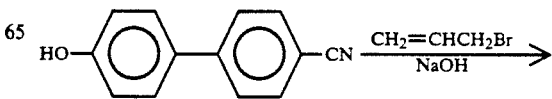

-continued

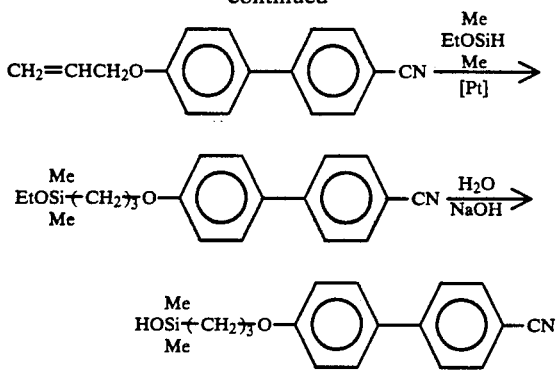

A solution prepared by dissolving 10.0 g (51.2 mmol) of 4-cyano-4'-hydroxybiphenyl in 100 ml of ethanol, was refluxed, and to this solution, 15 ml of an aqueous solution containing 3.7 g (66.1 mmol) of sodium hydroxide, was dropwise added. After completion of the dropwise addition, 13.3 ml (178 mmol) of allyl bromide was added thereto, and the mixture was stirred for about 1 hour, whereby a white solid precipitated in the solution. Ethanol was distilled off, and water was added to obtain a slurry. Then, the obtained solid was collected by filtration and purified by silica gel column chromatography to obtain 10.0 g of white crystals. With respect to the obtained product, $^1$H-NMR and IR spectrum analyses and elemental analysis were conducted to confirm that it was desired 4-allyloxy-4'-cyanobiphenyl. (yield: 83.0% melting point: 81° C.)

$^1$H-NMR spectrum, δ (CDCl$_3$, ppm): 4.59 (dr, 2H, CH$_2$=CHCH$_2$O—), 5.31 (dd, 1H, CH$_2$=CHCH$_2$O—), 5.42 (dd, 1H, CH$_2$=CHCH$_2$O—), 5.90–6.35 (m, 1H, CH$_2$=CHCH$_2$O—) 7.01 (d, 2H, proton peak of a phenylene group), 7.53 (d, 2H, proton peak of a phenylene group), 7.66 (s, 4H, proton peak of a phenylene group).

IR spectrum (cm$^{-1}$):
2950, 2880, 2230 (characteristic absorption by a C-N bond), 1605 (characteristic absorption by a phenylene group), 1495, 1290, 1180, 990, 830.

Elemental analysis (%): Found: C: 81.29, H: 5.61, N: 5.89. Calculated: C: 81.67, H: 5.57, N: 5.95.

8.10 g (34.4 mmol) of 4-allyloxy-4'-cyanobiphenyl thus obtained and 10.0 ml (72.2 mmol) of dimethylethoxysilane were dissolved in 60 ml of toluene, and 0.10 ml of an isopropyl alcohol solution of chloroplatinic acid (0.1 mol/l) was added thereto. The mixture was stirred overnight at 80° C. under an argon gas atmosphere. The solvent was distilled off, and the residue was purified by silica gel column chromatography to obtain 8.60 g of a colorless transparent liquid. With respect to the obtained product, $^1$H-NMR, IR and Mass spectrum analyses and elemental analysis were conducted to confirm that it was desired 4-(3-dimethylethoxysilylpropoxy)-4'-cyanobiphenyl. (yield: 73.6%)

$^1$H-NMR spectrum, a (CDCl$_3$, ppm): 0.15 (s 6H Si-CH$_3$), 0.53–0.83 (m, 2H, Si-CH$_2$CH$_2$CH$_2$—O), 1.20 (5, 3H, Si"OCH$_2$CH$_3$), 1.66–2.00 (m, 2H, Si-CH$_2$CH$_2$CH$_2$—O), 3.69 (q, 2H, Si—OCH$_2$CH$_3$), 3.99 (t, 2H, Si-CH$_2$CH$_2$CH$_2$—O), 6.99 (d, 2H, proton peak of a phenylene group), 7.50 (d, 2H, proton peak of a phenylene group), 7.66 (s, 4H, proton peak of a phenylene group)

IR spectrum (cm$^{-1}$): 2950, 2880, 2230 (characteristic absorption by a C-N bond), 1605 (characteristic absorption by a phenylene group), 1495, 1290, 1250 (characteristic absorption by a Si—C bond), 1180, 1105, 1075, 1000, 940, 890, 835.

Mass spectrum (m/e): 339 (M+), 297, 282, 103 (EtO-Me$_2$Si+).

Elemental analysis (%): Found: C: 70.63, H: 7.47, N: 4.05. Calculated: C: 70.76, H: 7.42, N: 4.13.

Then, 8.50 g (25.0 mmol) of this 4-(3-dimethylethoxysilylpropoxy)-4'-cyanobiphenyl was dissolved in 40 ml of ethanol. This solution was poured into a solution prepared by dissolving 5.0 g (125 mmol) of sodium hydroxide in 15 ml of water and 40 ml of methanol. Further, to this solution, an aqueous solution prepared by dissolving 5.0 g (125 mmol) of sodium hydroxide in 50 ml of water, was added. The mixture was stirred at room temperature for 15 minutes. Then, this reaction mixture was poured into an excess amount of ice water containing 35 g of potassium dihydrogen phosphate, and extracted with chloroform. Then, the organic layer was dried over anhydrous sodium sulfate. The solvent was distilled off, and the residue was purified by silica gel column chromatography to obtain 4.70 g of a white solid. With respect to the obtained product, $^1$H-NMR, IR and Mass spectrum analyses and elemental analysis were conducted to confirm that it was desired 4-(3-dimethylhydroxysilylpropoxy)-4'-cyanobiphenyl. (yield: 73.6%)

$^1$H-NMR spectrum, δ (CDCl$_3$, ppm): 0.12 (s, 6H, Si-CH$_3$), 0.60–0.81 (m, 2H, Si-CH$_2$CH$_2$CH$_2$—O), 1.65 (s, 1H, Si-OH), 1.70–2.00 (m, 2H, Si-CH$_2$CH$_2$CH$_2$—O), 4.00 (5, 2H, Si-CH$_2$CH$_2$CH$_2$—O), 7.00 (d, 2H, proton peak of a phenylene group), 7.50 (d, 2H, proton peak of a phenylene group), 7.68 (s, 4H, proton peak of a phenylene group)

IR spectrum (cm$^{-1}$): 3450 (characteristic absorption by a hydroxyl group), 2945, 2880, 2225 (characteristic absorption by a C—N bond), 1605 (characteristic absorption by a phenylene group), 1495, 1475, 1295, 1250 (characteristic absorption by a Si—C bond), 1180, 1050, 1030, 1010, 825.

Mass spectrum (m/e): 311 (M+), 269,254, 75 (HOMe$_2$Si+).

Elemental analysis (%): Found: C: 69.25, H: 6.72, N: 4.45. Calculated: C: 69.42, H: 6.80, N: 4.50.

EXAMPLE 2

Synthesis 1 of a monomer

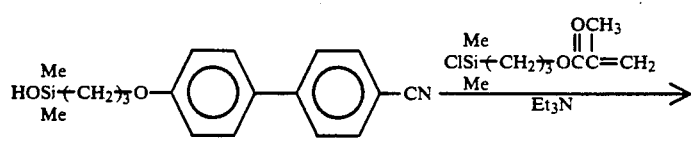

-continued

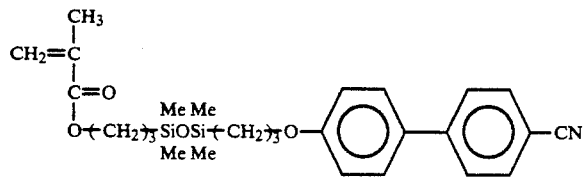

4.00 g (12.8 mmol) of 4-(3-dimethylhydroxysilylpropoxy)-4'-cyanobiphenyl obtained in Example 1, was dissolved in 10 ml of tetrahydrofuran under an argon gas atmosphere. To this solution, 2.20 ml (15.8 mmol) of triethylamine and 3.40 g (15.4 mmol) of 3-methacryloxypropyldimethylchlorosilane were added, and the mixture was stirred overnight at room temperature. A white salt formed, was filtered off while washing it with diethyl ether, and the solvent was distilled off. Then, the residue was purified by silica gel column chromatography to obtain 3.56 g of a colorless transparent liquid. With respect to the obtained product, 1H-NMR, IR and Mass spectrum analyses and elemental analysis were conducted to confirm that it was the monomer having the above structure. (yield: 56.0%).

$^1$H-NMR spectrum, δ (CDCl$_3$, ppm): 0.10 (s, 12H, Si—CH$_3$), 0.46–0.75 (m, 4H, Si—C$\overline{H_2}$CH$_2$CH$_2$—O×2), 1.53–1.87 (m, 4H, Si—CH$_2$C$\overline{H_2}$CH$_2$—O ×2), 1.96 (dd, 3H, CH$_2$=C(CH$_3$)COO—), 4.00 (t, 2H, Si—CH$_2$CH$_2$C$\underline{H_2}$—O), 4.13 (t, 2H, Si—CH$_2$CH$_2$CH$_2$—O), 5.53 (m, 1H, CH$_2$=C(CH$_3$)COO—), 6.60 (m, 1H, CH$_2$=C($\overline{CH_3}$)COO—), 6.98 (d, 2H, proton peak of a phenylene group), 7.53 (d, 2H, proton peak of a phenylene group), 7.66 (s, 4H, proton peak of a phenylene group)

IR spectrum (cm$^{-1}$): 2960, 2220 (characteristic absorption by a C—N bond), 1715 (characteristic absorption by a carboxyl group), 1635 (characteristic absorption by a C=C bond), 1605 (characteristic absorption by a phenyl group), 1495, 1475, 1400, 1320, 1295, 1250 (characteristic absorption by a Si—C bond), 1170, 1050 (characteristic absorption by a siloxane bond), 940, 820, 800.

Mass spectrum (m/e): 495 (M+), 326,259,217, 69 (CH$_2$=C(CH$_3$)CO+), 41 (CH$_2$=C(CH$_3$)+).

Elemental analysis (%): Found: C: 65.30, H: 7.50, N: 2.68. Calculated: C: 65.41, H: 7.52, N: 2.83.

EXAMPLE 3

Synthesis 1 of a polymer

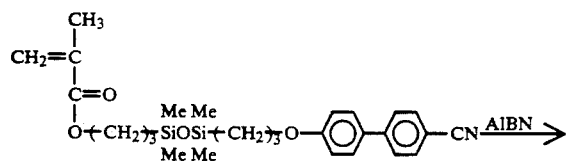

Polymer 1.50 (3.02 mmol) of the monomer obtained in Example 2 was dissolved in 15 ml of tetrahydrofuran. To this solution, 25 mg (0.152 mmol) of azobisisobutyronitrile was added (monomer concentration: about 200 mmol/l, initiator concentration: about 10 mmol/l). This solution was thoroughly freeze-dearated. Then, a polymerization reaction was conducted at 60° C. for 24 hours. The reaction solution was poured into 250 ml of methanol, and the formed precipitate was recovered and dissolved in tetrahydrofuran, and reprecipitation from methanol was repeated twice. As a result, 0.92 g of a white solid polymer was obtained (yield: 61.0%). With respect to the obtained polymer, $^1$H-NMR and IR spectrum analyses and elemental analysis were conducted to confirm that it was a polymer wherein the repeating units were represented by the formula:

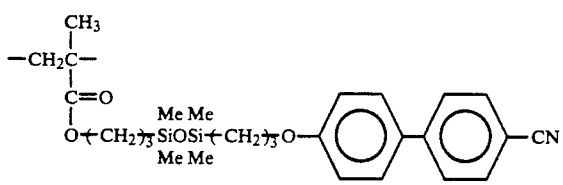

The number average molecular weight and the weight average molecular weight obtained by gel permeation chromatography were 1.18×10$^4$ and 2.11×10$^4$ respectively, as polystyrene standards. The glass transition temperature of this polymer was −14° C.

$^1$H-NMR spectrum, δ (CDCl$_3$, ppm): 0.10 (s, 12H, Si—CH$_3$), 0.38–0.80 (m, 4H, Si≧C$\overline{H_2}$CH$_2$CH$_2$—O×2), 0.85–1.10 (m, 3H, —CH$_2$C(CH$_3$)—), 1.45–2.28 (m, 6H, Si—CH$_2$CH$_2$CH$_2$—O×2, —$\overline{CH_2}$C(CH$_3$)—), 3.98 (t, 4H, Si—C$\overline{H_2}$CH$_2$CH$_2$—O×2), 7.00 (d, 2H, proton peak of a phenylene group), 7.53 (d, 2H, proton peak of a phenylene group), 7.65 (s, 4H, proton peak of a phenylene group).

IR spectrum (cm$^{-1}$): 2960, 2220 (characteristic absorption by a C—N bond), 1715 (characteristic absorption by a carboxyl group), 1605 (characteristic absorption by a phenyl group), 1495, 1475, 1400, 1320, 1295, 1250 (characteristic absorption by a Si—C bond), 1170, 1050 (characteristic absorption by a siloxane bond), 940, 820, 800.

Elemental analysis (%): Found: C: 65.40, H: 7.61, N: 2.87. Calculated: C: 65.41, H: 7.52, N: 2.83.

EXAMPLE 4

Synthesis 2 of a monomer

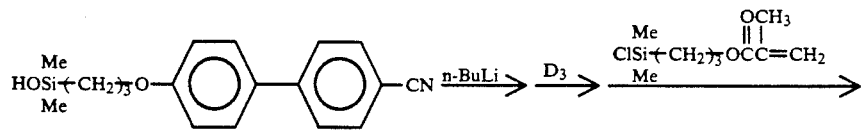

-continued

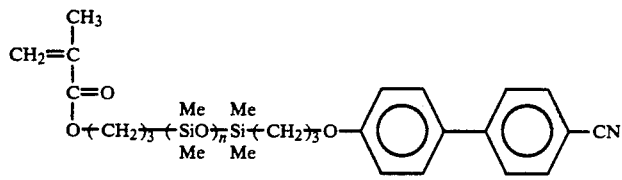

2.00 g (6.42 mmol) of 4-(3-dimethylhydroxysilyl-propoxy)-4'-cyanobiphenyl obtained in Example 1 was dissolved in 20 mg of tetrahydrofuran under an argon gas atmosphere. This solution was cooled to −78° C., and then 4.05 ml (6.48 mmol) of a hexane solution of n-butyllithium (1.6 mol/g) was added thereto, and the mixture was stirred for 2 hours. To this solution, a solution prepared by dissolving 1.43 g (6.43 mmol) of hexamethylcyclotrisiloxane in 20 ml of tetrahydrofuran, was added, and the mixture was heated to room temperature and further stirred overnight. Then, 2.13 g (9.63 mmol) of 3-methacryloxy propyldimethylchlorosilane was added thereto to terminate the reaction. A white salt formed, was filtered off while washing it with diethyl ether, and the solvent was distilled off. Then, the residue was purified by silica gel column chromatography to obtain 2.90 g of a colorless white liquid.

With respect to the product, $^1$H-NMR and IR spectrum analyses were conducted to confirm that it was a monomer having the above structure. The product was substantially the same as the monomer obtained in Example 1 with respect to both $^1$H-NMR and IR spectra except that in the $^1$H-NMR spectrum, the area of the proton peak of the methyl group on silicon appearing at 0.10 ppm was about 2.4 times. However, in this case, the average polymerization degree $\bar{n}$ of the polysiloxane bond obtained from the ratio of the peak area of the $^1$H-NMR spectrum was 2.8.

EXAMPLE 5

Synthesis 2 of a polymer

Using 1.60 g of the monomer obtained in Example 4, the polymerization reaction and purification were conducted in the same manner as in Example 3 to obtain 1.06 g of a colorless rubber-like polymer. (yield: 66.2%).

With respect to the obtained polymer, $^1$H-NMR and IR spectrum analyses were conducted to confirm that it was a polymer in which the repeating units were represented by the formula:

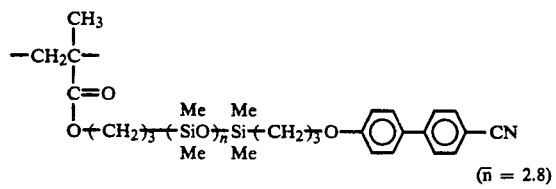

($\bar{n}$ = 2.8)

The product was substantially the same as the polymer obtained in Example 2 with respect to both the $^1$H-NMR and IR spectra except that in the $^1$H-NMR spectrum, the area of the proton peak of the methyl group on silicon appearing at 0.10 ppm was about 2.4 times. The number average molecular weight and the weight average molecular weight obtained by gel permeation chromatography were 2.59×10$^4$ and 5.62×10$^4$, respectively, as polystyrene standards. The glass transition temperature of this polymer was −32° C.

EXAMPLE 6

Synthesis 3 of a monomer

In the same manner as in Example 4 except that in the monomer synthesis described in Example 4, the amount of hexamethylcyclotrisiloxane was changed to 2.86 g (12.9 mmol), 4.50 g of a colorless transparent liquid was obtained.

With respect to the obtained product, $^1$H-NMR and IR spectrum analyses were conducted to confirm that it was a monomer having the structure as shown in Example 4. The product was substantially the same as the monomer obtained in Example 4 with respect to both the $^1$H-NMR and IR spectra except that in the $^1$H-NMR, the area of the proton peak of the methyl group on silicon appearing at 0.10 ppm was about 3.9 times. However, in this case, the average polymerization degree $\bar{n}$ of the polysiloxane bond obtained from the ratio of the peak area of the $^1$H-NMR spectrum was 5.8.

EXAMPLE 7

Synthesis 3 of a polymer

Using 1.5 g of the monomer obtained in Example 6, the polymerization reaction and purification were conducted in the same manner as in Example 3 to obtain 1.02 g of a colorless rubber-like polymer. (yield: 68.0%)

With respect to the obtained polymer, $^1$H-NMR and IR spectrum analyses were conducted to confirm that it was a polymer in which the repeating units were represented by the formula:

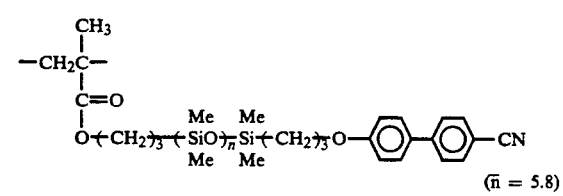

($\bar{n}$ = 5.8)

The polymer was substantially the same as the polymer obtained in Example 5 with respect to both the $^1$H-NMR and IR spectra except that in the $^1$H-NMR spectrum, the area of the proton peak of the methyl group on silicon appearing at 0.10 ppm was about 3.9 times. The number average molecular weight and the weight average molecular weight obtained by gel permeation chromatography were 2.82×10$^4$ and 6.05×10$^4$, respectively, as polystyrene standards. The glass transition temperature of this polymer was −54° C.

EXAMPLE 8

Synthesis 2 of a silanol compound having a mesogenic group

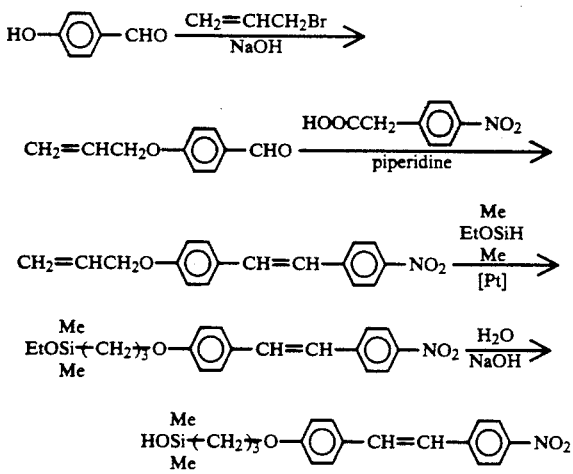

25.0 g (205 mmol) of p-hydroxybenzaldehyde, 30 ml (347 mmol) of allyl bromide and 6.5 g (19.1 mmol) of tetrabutylammoniumhydrogen sulfate, were dissolved in 60 ml of tetrahydrofuran. To this solution, 17 ml of an aqueous solution containing 16.5 g of sodium hydroxide was added. The mixture was stirred at room temperature for 2 hours. Then, this reaction solution was poured into an excess amount of water and extracted with diethyl ether. Then, the organic layer was dried over anhydrous sodium sulfate. The solvent was distilled off, and the residue was purified by silica gel column chromatography to obtain 28.0 g of a yellow solid. With respect to the obtained product, $^1$H-NMR spectrum analysis was conducted to confirm that it was desired p-allyloxybenzaldehyde. (yield: 84.2%, melting point: 22° C.).

$^1$H-NMR spectrum, δ (CDCl$_3$, ppm): 4.65 (dt, 2H, CH$_2$=CHC$\underline{H_2}$O—), 5.32 (dd, 1H, C$\underline{H_2}$=CHCH$_2$O—), 5.45 (dd, 1H, C$\underline{H_2}$=CHCH$_2$O—), 5.88-6.30 (m, 1H, CH$_2$=C$\underline{H}$CH$_2$O—), 7.00 (d, 2H, proton peak of a phenylene group), 7.83 (d, 2H, proton peak of a phenylene group), 9.86 (s, proton peak of a aldehyde group).

To 30.8 g (170 mmol) of p-nitrophenylacetic acid, 17 ml (172 mmol) of piperidine was dropwise added at room temperature under an argon gas atmosphere. Further, 16.0 g (98.7 mmol) of p-allyloxybenzaldehyde was added thereto, and the mixture was stirred at 100° C. for 2 hours. The stirring was continued for further 3 hours at 130° C., whereby a brown solid formed in the reaction solution. This reaction mixture was heated and stirred at 100° C. under a reduced pressure of about 1 mmHg to distill off piperidine and other byproducts, and an obtained solid was purified by silica gel column chromatography to obtain 19.2 g of a yellow solid. With respect to the product, $^1$H-NMR and IR spectrum analyses and elemental analysis were conducted to confirm that it was desired 4-allyloxy-4'-nitrostilbene (yield: 69.2% melting point: 114° C.).

$^1$H-NMR spectrum, δ (CDCl$_3$, ppm): 4.62 (dt, 2H, CH$_2$=CHC$\underline{H_2}$O—), 5.33 (dd, 1H, C$\underline{H_2}$=CHCH$_2$O—), 5.46 (dd, 1H, C$\underline{H_2}$=CHCH$_2$O—), 5.91-6.30 (m, 1H, CH$_2$=C$\underline{H}$CH$_2$O—), 6.90-7.25 (m, 4H, proton peak of a phenylene group), 7.41-7.70 (m, 4H, proton peak of a phenylene group), 8.24 (d, 2H, proton peak of a vinylene group), IR spectrum (cm$^{-1}$): 2850, 2730, 1595 (characteristic absorption by a phenylene group), 1510 (characteristic absorption by a nitro group), 1340 (characteristic absorption by a nitro group), 1270, 1160, 995, 930, 830.

Elemental analysis (%): Found: C: 72.61, H: 5.33, N: 4.90. Calculated: C: 72.58, H: 5.38, N: 4.98.

To 5.0 g (17.8 mmol) of 4-allyloxy-4'-nitrostilbene thus obtained, 1.5 g of 5% platinum-carbon was added, and the mixture was dissolved in 30 ml of toluene. Then, 10.0 ml (72.2 mmol) of dimethylethoxysilane was added thereto under an argon gas atmosphere, and the mixture was stirred at 50° C. for 3 hours. To this solution, diethyl ether was added, and the mixture was filtered, and the solvent was distilled off. The residue was purified by silica gel column chromatography to obtain 4.80 g of a yellow solid. With respect to the obtained product, $^1$H-NMR IR and Mass spectrum analyses and elemental analysis were conducted to confirm that it was desired 4-(3-dimethylethoxysilylpropoxy)-4'-nitrostilbene. (yield: 70.0%).

$^1$H-NMR spectrum, δ (CDCl$_3$, ppm): 0.15 (s, 6H, Si—CH$_3$), 0.63-0.82 (m, 2H, Si—C$\underline{H_2}$CH$_2$CH$_2$—O), 1.20 (t, 3H, Si—OCH$_2$C$\underline{H_3}$), 1.66-2.00 (m, 2H, Si—CH$_2$C$\underline{H_2}$CH$_2$—O), 2.69 (q, 2H, Si—OC$\underline{H_2}$CH$_3$), 3.97 (t, 2H, Si—CH$_2$CH$_2$C$\underline{H_2}$—O), 6.86-7.16 (m, 4H, proton peak of a phenylene group), 7.43-7.63 (m, 4H, proton peak of a phenylene group), 8.20 (d, 2H, proton peak of a vinylene group).

IR spectrum (cm$^{-1}$): 2950, 2880, 1590 (characteristic absorption by a phenylene group), 1510 (characteristic absorption by a nitro group), 1340 (characteristic absorption by a nitro group), 1250 (characteristic absorption by a Si—C bond), 1175, 1110, 1030, 940, 890, 835.

Mass spectrum (m/e): 385 (M$^+$), 343, 328, 103 (EtOMe$_2$Si+).

Elemental analysis (%): Found: C: 65.32, H: 6.96, N: 3.74. Calculated: C: 65.42, H: 7.06, N: 3.63.

2.40 g (62.0 mmol) of 4-(3-dimethylethoxysilylpropoxy)-4'-nitrostilbene thus obtained, was dissolved in 15 ml of ethanol and 6 ml of tetrahydrofuran. This solution was poured into a solution prepared by dissolving 2.0 g (50 mmol) of sodium hydroxide in 2 ml of water and 15 ml of methanol. To this solution, an aqueous solution prepared by dissolving 2.0 g (50 mmol) of sodium hydroxide in 10 ml of water, was further added. The mixture was stirred at room temperature for 10 minutes. Then, this reaction mixture was poured into an excess amount of ice water containing 6.8 g of potassium dihydrogen phosphate and extracted with chloroform. Then, the organic layer was dried over anhydrous sodium sulfate. The solvent was distilled off, and the residue was purified by silica gel column chromatography to obtain 1.50 g of a yellow solid. With respect to the obtained product, $^1$H-NMR IR and Mass spectrum analyses and elemental analysis were conducted to confirm it was desired 4-(3-dimethylhydroxysilylpropoxy)-4'-nitrostilbene. (yield: 67.7%).

$^1$H-NMR spectrum, δ (CDCl$_3$, ppm): 0.18 (s, 6H, Si—CH$_3$), 0.66-0.84 (m, 2H, Si—C$\underline{H_2}$CH$_2$CH$_2$—O), 1.69 (s, 1H, Si—O$\underline{H}$), 1.81-2.00 (m, 2H, Si—CH$_2$C$\underline{H_2}$CH$_2$—O), 4.00 (t, 2H, Si—CH$_2$CH$_2$C$\underline{H_2}$—O), 6.87-7.16 (m, 4H, proton peak of a phenylene group), 7.44-7.64 (m, 4H, proton peak of a phenylene group), 8.20 (d, 2H, proton peak of a vinylene group).

IR spectrum (cm$^{-1}$): 3280 (characteristic absorption by a hydroxyl group), 2950, 2880, 1590 (characteristic absorption by a phenylene group), 1510 (characteristic absorption by a nitro group), 1340 (characteristic absorption by a nitro group), 1250 (characteristic absorption by a Si—C bond), 1180, 1105, 1030, 970, 870, 840.

Mass spectrum (m/e): 357 (M+), 315, 300, 75 (HOMe₂Si+)

Elemental analysis (%): Found: C: 63.90, H: 6.38, N: 3.90. Calculated: C: 63.84, H: 6.49, N: 3.92.

EXAMPLE 9

Synthesis 4 of a monomer

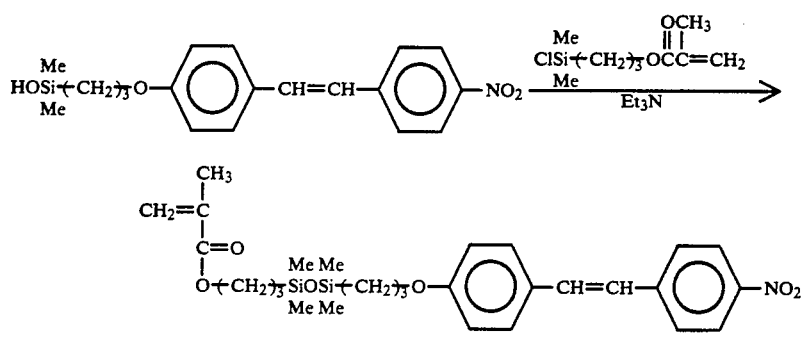

2.00 g (5.60 mmol) of 4-(3-dimethylhydroxysilyl-propoxy)-4'-nitrostilbene obtained in Example 8 was dissolved in 10 ml of tetrahydrofuran under an argon atmosphere. To this solution, 1.56 ml (11.2 mmol) of triethylamine and 1.24 g (5.62 mmol) of 3-methacryloxypropyldimethylchlorosilane were added, and the mixture was stirred overnight at room temperature. A white salt formed, was filtered off while washing it with diethyl ether. The solvent was distilled off, and the residue was purified by silica gel column chromatography to obtain 2.40 g of a yellow solid. With respect to the product, ¹H-NMR, IR and Mass spectrum analyses and elemental analysis were conducted to confirm that it was a monomer having the above structure. (yield: 79.1%). ¹H-NMR spectrum, δ (CDCl₃, ppm): 0.10 (s, 12H, Si—CH₃), 0.35-0.70 (m, 4H, Si—CH₂CH₂CH₂—O×2), 1.52-1.93 (m, 4H, Si—CH₂CH₂CH₂—O×2), 1.94 (dd, 3H, CH₂=C(CH₃)COO—), 3.96 (t, 2H, Si—CH₂CH₂CH₂—O), 4.10 (t, 2H, Si—CH₂CH₂CH₂—O), 5.54 (m, 1H, CH₂=C(CH₃)COO—), 6.10 (m, 1H, CH₂=C(CH₃)COO—), 6.89-7.15 (m, 4H, proton peak of a phenylene group), 7.48-7.68 (m, 4H, proton peak of a phenylene group), 8.27 (d, 2H, proton peak of a vinylene group).

IR spectrum (cm⁻¹): 2950, 2890, 1770 (characteristic absorption by a carbonyl group), 1635 (characteristic absorption by a C=C bond), 1590 (characteristic absorption by a phenylene group), 1510 (characteristic absorption by a nitro group), 1340 (characteristic absorption by a nitro group), 1250 (characteristic absorption by a Si—C bond), 1175, 1110, 1050 (characteristic absorption by a siloxane bond), 970, 840, 800.

Mass spectrum (m/e): 541 (M+), 248, 217, 69 (CH₂=C(CH₃)CO+), 41 (CH₂=C (CH₃)+).

Elemental analysis (%): Found: C: 62.01, H: 7.22, N: 2.55. Calculated: C: 62.07, H: 7.26, N: 2.59.

EXAMPLE 10

Synthesis 4 of a polymer

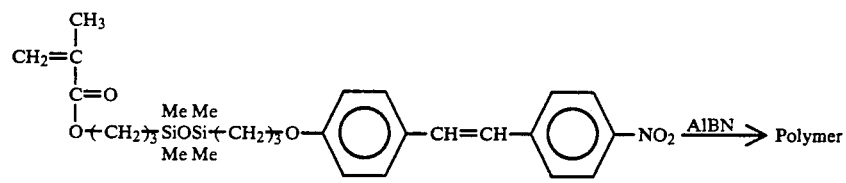

Using 2.04 g (3.76 mmol) of the monomer obtained in Example 9, the polymerization reaction and purification were conducted in the same manner as in Example 3 to obtain 1.45 g of a yellow solid polymer (yield: 71.1%). With respect to the obtained polymer, ¹H-NMR and IR spectrum analyses and elemental analysis were conducted to confirm that it was a polymer wherein the repeating units were represented by:

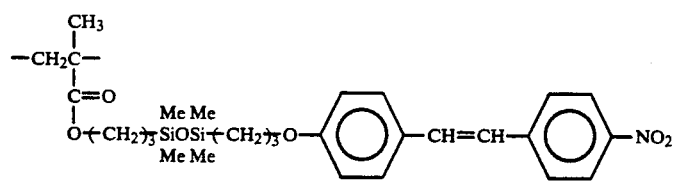

The number average molecular weight and the weight average molecular weight obtained by gel permeation chromatography were 4.05×10⁴ and 8.91×10⁴ respectively, as polystyrene standards. The glass transition temperature of this polymer was 61° C.

¹H-NMR spectrum, δ (CDCl₃, ppm): 0.10 (s, 12H, Si—CH₃), 0.50-0.80 (m, 4H, Si—CH₂CH₂CH₂—O×2), 0.85-1.10 (m, 3H, —CH₂C(CH₃)—), 1.48-2.15 (m, 6H, Si—CH₂CH₂CH₂—O×2 and —CH₂C(CH₃)—), 4.00 (t, 2H, Si—CH₂CH₂CH₂—O), 4.15 (t, 2H, Si—CH₂CH₂CH₂—O), 6.85-7.16 (m, 4H, proton peak of a phenylene group), 7.46-7.65 (m, 4H, proton peak of a phenylene group), 8.20 (d, 2H, proton peak of a vinylene group).

IR spectrum (cm$^{-1}$): 2950, 2880, 1715 (characteristic absorption by a carbonyl group), 1590 (characteristic absorption by a phenylene group), 1510 (characteristic absorption by a nitro group), 1340 (characteristic absorption by a nitro group), 1250 (characteristic absorption by a Si—C bond), 1175, 1110, 1050 (characteristic absorption by a siloxane bond), 970, 840, 800.

Elemental analysis (%): Found: C: 61.98, H: 7.34, N: 2.51. Calculated: C: 62.07, H: 7.26, N: 2.59.

EXAMPLE 11

Synthesis 3 of a silanol compound having a mesogenic group

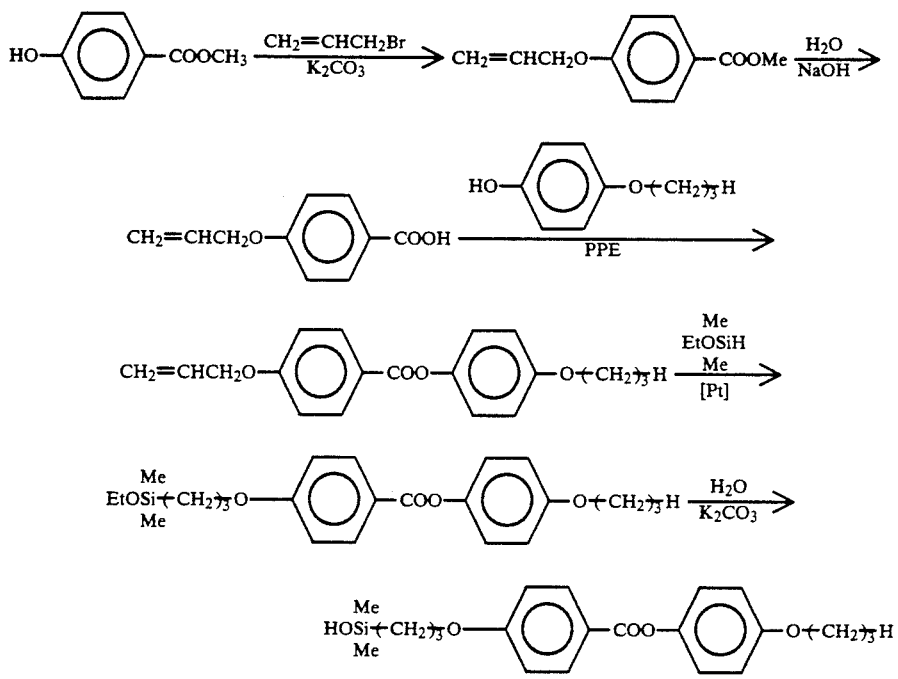

15.0 g (98.6 mmol) of methyl p-hydroxybenzoate and 13.0 g (94.1 mmol) of potassium carbonate were mixed in 150 ml of acetone to obtain a solution. To this solution, 13 ml (150 mmol) of allyl bromide was added, and the mixture was stirred at 80° C. for 2 hours under an argon gas atmosphere. To this solution, water was added, and the mixture was extracted with ethyl acetate. Then, the organic layer washed sequentially with a 5% sodium hydroxide aqueous solution and a saturated sodium chloride aqueous solution. The solvent was distilled off, and then the residue was purified by silica gel column chromatography to obtain 18.6 g of colorless transparent liquid. With respect to the obtained product, $^1$H-NMR IR and Mass spectrum analyses were conducted to confirm that it was desired methyl p-allyloxybenzoic acid. (yield: 96.6%).

$^1$H-NMR spectrum, δ (CDCl$_3$, ppm): 3.88 (s, 3H, —COOCH$_3$), 4.58 (dt, 2H, CH$_2$=CHCH$_2$O—), 5.32 ( dd, 1H, CH$_2$=CHCH$_2$O—), 5.43 ( dd, 1H, CH$_2$=CHCH$_2$O—), 5.86–6.22 (m, 1H, CH$_2$=CHCH$_2$O—), 6.92 (d, 2H, proton peak of a phenylene group), 7.98 (d, 2H, proton peak of a phenylene group).

IR spectrum (cm$^{-1}$): 2960, 1720 (characteristic absorption by a carbonyl group), 1610 (characteristic absorption by a phenylene group), 1510 1435, 1280, 1255, 1170, 1110, 1020, 845, 770.

Mass spectrum (m/e): 192 (M+), 161, 41 (CH$_2$=CHCH$_2$+). 18.0 g (93.6 mmol) of methyl p-allyloxybenzoate obtained here, was dissolved in 600 ml of ethanol. This solution was poured into a solution prepared by dissolving 12.0 g (300 mmol) of sodium hydroxide in 80 ml of water and 100 ml of methanol, and the mixture was further refluxed at 80° C. for 2 hours. The solvent was distilled off, and the obtained white solid was dissolved in water, and hydrochloric acid was added until the solution became acidic, whereby a white precipitate formed. This was extracted with methylene chloride, and the organic layer was washed with a saturated sodium chloride aqueous solution and then dried over anhydrous magnesium sulfate. The solvent was distilled off, and the residue was purified by silica gel column chromatography to obtain 14.7 g of a white solid. With respect to the obtained product, $^1$H-NMR IR and Mass spectrum analyses were conducted to confirm that it was desired p-allyloxybenzoic acid. (yield: 88.1%).

$^1$H-NMR spectrum, δ (CDCl$_3$, ppm): 4.56 (dt, 2H, CH$_2$=CHCH$_2$O—), 5.27 (dd, 1H, CH$_2$=CHCH$_2$O—), 5.43 (dd, 1H, CH$_2$=CHCH$_2$O—), 5.84–6.28 (m, 1H, CH$_2$=CHCH$_2$O—), 6.90 (d, 2H, proton peak of a phenylene group), 7.95 (d, 2H, proton peak of a phenylene group).

IR spectrum (cm$^{-1}$): 2450–3000 (characteristic absorption by a hydroxyl group of a carboxylic acid), 1680 (characteristic absorption by a carbonyl group), 1600 (characteristic absorption by a phenylene group), 1550, 1430, 1350, 1250, 1180, 1010, 1000, 930, 850, 770.

Mass spectrum (m/e): 178 (M+), 41 (CH$_2$=CHCH$_2$+).

To 90 g of phosphorus pentoxide, 100 ml of chloroform and 200 ml of diethyl ether were added, and the mixture was refluxed at 60° C. for 2 days under an argon atmosphere. Then, the solvent was distilled off to obtain polyphosphoric acid ester (hereinafter referred to simply as PPE) as a viscous colorless liquid. 30.0 g of this PPE, 5.00 g (28.1 mmol) of p-allyloxybenzoic acid and 4.40 g of (28.9 mmol) of p-propoxyphenol were dissolved in 100 ml of chloroform under an argon gas atmosphere, and the solution was stirred overnight at room temperature. Water was added thereto, and the mixture was extracted with methylene chloride. The organic layer was dried over anhydrous sodium sulfate, and the solvent was distilled off. Then, the residue was purified by silica gel column chromatography to obtain 8.30 g of a white solid. With respect to the obtained product, 1H-NMR IR and Mass spectrum analyses and elemental analyses were conducted to confirm that it was desired p-propoxyphenyl p-allyloxybenzoate. (yield: 94.6% melting point: 71° C.)

1H-NMR spectrum, δ (CDCl3, ppm): 1.05 ( t, 3H, —OCH2CH2CH3 ), 1.70:1.94 (m, 2H, —OCH2CH2CH3), 3.93 (t, 2H, —OCH2CH2CH3), 4.63 (dt, 2H, CH2=CHCH2O—), 5.36 ( dd, 1H, CH2=CHCH2O—), 5.43 (dd, 1H, CH2=CHCH2O—), 5.88–6.13 (m, 1H, CH2=CHCH2O—), 6.85–7.16 (m, 6H, proton peak of a phenylene group), 8.14 (d, 2H, proton peak of a phenylene group).

IR spectrum (cm−1): 2950, 1725 (characteristic absorption by a carbonyl group), 1605 (characteristic absorption by a phenylene group), 1515, 1480, 1460, 1430, 1320, 1310, 1280, 1260, 1170, 1080, 1020, 940, 850, 800, 760.

Mass spectrum (m/e): 312 (M+), 279, 161, 41 (CH2=CHCH2+).

Elemental analysis (%): Found: C: 73.04, H: 6.41 Calculated: C: 73.06, H: 6.45.

3.50 g (11.2 mmol) of p-propoxyphenyl p-allyloxybenzoate thus obtained and 7.0 ml (50.9 mmol) of dimethylethoxysilane were dissolved in 120 ml of tetrahydrofuran, and 0.10 ml of a methylene chloride solution of dicyclopentadienylplatinum dichloride (0.1 mol/l) was added thereto. The mixture was stirred overnight at 50° C. under an argon gas atmosphere. The solvent was distilled off, and the residue was purified by silica gel column chromatography to obtain 3.51 g of a colorless transparent liquid. With respect to the obtained product, 1H-NMR, IR and Mass spectrum analyses and elemental analyses were conducted to confirm that it was desired p-propoxyphenyl p-(3-dimethylethoxysilylpropoxy)benzoate. (yield: 75.2%).

1H-NMR spectrum, δ (CDCl3, ppm): 1.05 (s, 6H, Si—CH3), 0.64–0.93 (m, 2H, Si—CH2CH2CH2—O), 1.04 (t, 3H, —OCH2CH3), 1.20 (t, 3H, Si—OCH2CH3), 1.70–2.16 (m, 4H, Si—CH2CH2CH2—O —OCH2CH2CH3), 3.69 (q, 2H, Si—OCH2CH3), 3.93 (t, 2H, Si—CH2CH2CH2—O), 4.12 (t, 2H,—OCH2CH2CH3), 6.86–7.16 (m, 6H, proton peak of a phenylene group), 8.12 (d, 2H, proton peak of a phenylene group).

IR spectrum (cm−1): 2950, 2880, 1730 (characteristic absorption by a carbonyl group), 1610 (characteristic absorption by a phenylene group), 1580, 1480, 1400, 1320, 1260 (characteristic absorption by a Si—C bond), 1190, 1010, 980 , 950 , 850 , 800 , 770.

Mass spectrum (m/e): 416 (M+), 265, 161, 145, 103 (EtOMe2Si+), 59 (CH3CH2CH2O+).

Elemental analysis (%): Found: C: 66.23, H: 7.72. Calculated: C: 66.31, H: 7.74.

3.50 g (8.40 mmol) of p-propoxyphenyl p-(3-dimethylethoxysilylpropoxy)benzoate thus obtained was dissolved in 100 ml of acetone. This solution was poured at 0° C. into a solution prepared by dissolving 3.5 g (25.3 mmol) of potassium carbonate in 30 ml of water and 100 ml of acetone. To this solution, an aqueous solution prepared by dissolving 3.5 g (25.3 mmol) of potassium carbonate in 100 ml of water, was further added. The mixture was stirred at 0° C. for 2 hours. Then, this reaction mixture was poured into an excess amount of ice water containing 8.0 g of potassium dihydrogen phosphate and extracted with methylene chloride. Then, the organic layer was dried over anhydrous sodium sulfate. The solvent was distilled off, and the residue was purified by silica gel column chromatography to obtain 2.68 g of a white solid. With respect to the obtained product, 1H-NMR, IR and Mass spectrum analyses and elemental analysis were conducted to confirm that it was desired p-propoxyphenyl p-(3-dimethylhydroxysilylpropoxy) benzoate. (yield: 82.2%).

1H-NMR spectrum, δ (CDCl3, ppm): 0.19 (s, 6H, Si—CH3), 0.66–0.85 (m, 2H, Si—CH2CH2CH2O), 1.04 ( t, 3H, —OCH2CH2CH3), 1.64 ( s, 1H, Si—OH), 1.66–2.00 (m, 4H, Si—CH2CH2CH2—O, —OCH2CH2CH3), 3.93 (t, 2H, Si—CH2CH2CH2—O), 4.03 (t, 2H, —OCH2CH2CH3), 6.85–7.16 (m, 6H, proton peak of a phenylene group), 8.13 (d, 2H, proton peak of a phenylene group).

IR spectrum (cm−1): 3450 (characteristic absorption by a hydroxyl group), 2980, 2900, 1720 (characteristic absorption by a carbonyl group), 1650 (characteristic absorption by a phenylene group), 1440, 1320, 1280, 1260 (characteristic absorption by a Si—C bond), 1200, 1170, 1110, 1080, 1010, 900, 850.

Mass spectrum (m/e): 388 (M+), 237, 195, 121, 75 (HOMe2Si+)

Elemental analysis (%): Found: C: 64.80, H: 7.33. Calculated: C: 64.92, H: 7.26.

EXAMPLE 12

Synthesis 5 of a monomer

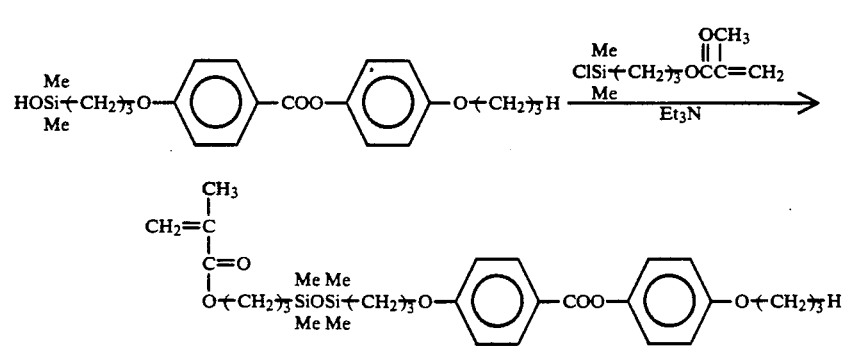

1.50 g (3.86 mmol) of p-propoxyphenyl p-(d-dimethylhydroxysilylpropoxy)benzoate obtained in Example 11, was dissolved in 10 ml of tetrahydrofuran under an argon gas atmosphere. To this solution, 0.65 ml (4.66 mmol) of triethylamine and 1.00 g (4.53 mmol) of 3-methacryloxypropyldimethylchlorosilane were added, and the mixture was stirred overnight at room temperature. A white salt formed was filtered off while washing it with diethyl ether. The solvent was distilled off, and the residue was purified by silica gel column chromatography to obtain 2.00 g of a slightly yellow liquid.

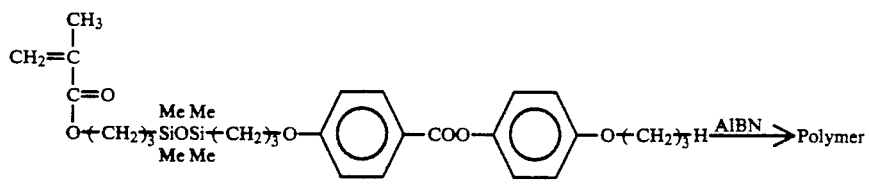

With respect to the obtained product, $^1$H-NMR IR and Mass spectrum analyses and elemental analysis were conducted to confirm that it was a monomer having the above structure. (yield: 90.5%). $^1$H-NMR spectrum, δ (CDCl$_3$, ppm):

0.10 (s, 12H, Si—CH$_3$), 0.47-0.75 (m, 4H, Si—CH$_2$CH$_2$CH$_2$O×2), 1.04 ( t, 3H, —OCH$_2$CH$_2$CH$_3$), 1.57-1.96 (m, 9H, Si—CH$_2$CH$_2$CH$_2$—O×2, —OCH$_2$CH$_2$CH$_3$, CH$_2$=C(CH$_3$)COO—) , 3.93 (t, 4H, Si—CH$_2$CH$_2$CH$_2$—O×2), 4.05 (t, 2H, —OCH$_2$CH$_2$CH$_3$), 5.54 ( m, 1H, CH$_2$=C(CH$_3$)COO—), 6.10 (m, 1H, CH$_2$=C(CH$_3$)COO—), 6.85-7.16 (m, 6H, proton peak of a phenylene group), 8.12 (d, 2H, proton peak of a phenylene group).

IR spectrum (cm$^{-1}$): 2990, 2900, 1740 (characteristic absorption by a carbonyl group), 1650 (characteristic absorption by a phenylene group), 1615 (characteristic absorption by a C=C bond), 1520 (characteristic absorption by a phenylene group), 1260 (characteristic absorption by a Si—C bond), 1170, 1080, 1055 (characteristic absorption by a siloxane bond), 850, 800.

Mass spectrum (m/e): 572 (M+), 421, 279, 217, 69 (CH$_2$=C(CH$_3$)CO+), 41 (CH$_2$C(CH$_3$)+).

Elemental analysis (%): Found: C: 62.78, H: 7.71. Calculated: C: 62.90, H: 7.74.

EXAMPLE 13

Synthesis 5 of a polymer

Using 1.90 g (3.32 mmol) of the monomer obtained in Example 12, the polymerization reaction and purification were conducted in the same manner as in Example 3 to obtain 1.51 g of a white polymer (yield: 79.5%). With respect to the obtained polymer, $^1$H-NMR and IR spectrum analyses and elemental analysis were conducted to confirm that it was a polymer wherein the repeating units were represented by the formula:

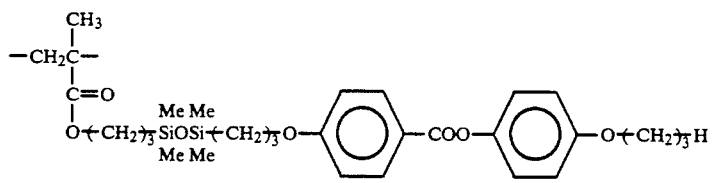

The number average molecular weight and the weight average molecular weight obtained by gel permeation chromatography were 4.26×10$^4$ and 1.06×10$^5$, respectively, as polystyrene standards. The grass transition temperature of this polymer was 25° C. The glass transition temperature of this polymer was −3° C. $^1$H-NMR spectrum, δ (CDCl$_3$, ppm): 0.10 (s, 12H, Si—CH$_3$), 0.45-0.80 (m, 4H, Si—CH$_2$CH$_2$CH$_2$—O, ×2), 0.85-1.10 (m, 6H, —CH$_2$C(CH$_3$)—, —OCH$_2$CH$_2$CH$_3$), 1.48-2.15 (m, 8H, Si—CH$_2$CH$_2$CH$_2$—O×2, —OCH$_2$CH$_2$CH$_3$, —CH$_2$C(CH$_3$)—), 3.94 (5, 4H, Si—CH$_2$CH$_2$CH$_2$—O×2), 4.05 (t, 2H, —OCH$_2$CH$_2$CH$_3$), 6.85-7.16 (m, 6H, proton peak of a phenylene group), 8.12 (d, 2H, proton peak of a phenylene group).

IR spectrum (cm$^{-1}$): 2990, 2900, 1730 (characteristic absorption by a carbonyl group), 1650 (characteristic absorption by a phenylene group), 1520 (characteristic absorption by a phenylene group), 1250 (characteristic absorption by a Si—C bond), 1170, 1080, 1055 (characteristic absorption by a siloxane bond), 850,800.

Elemental analysis (%): Found: C: 62.72, H: 7.80. Calculated: C: 62.90, H: 7.74.

EXAMPLE 14

Synthesis 4 of a silanol compound having a mesogenic group

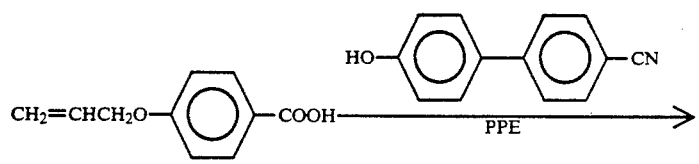

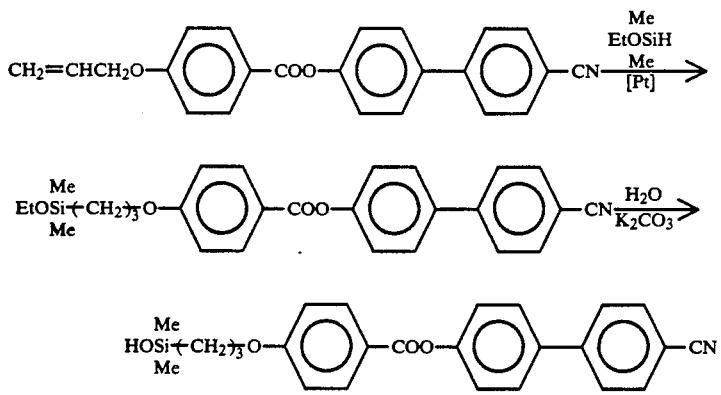

30.0 g of PPE, 5.00 g (28.1 mmol) of p-allyloxybenzoic acid and 5.60 g (28.7 mmol) of 4-cyano-4'-hydroxybiphenyl were dissolved in 120 ml of chloroform under an argon gas atmosphere, and the solution was stirred overnight at room temperature. Water was added hereto, and the mixture was extracted with methylene chloride. The organic layer was dried over anhydrous sodium sulfate. The solvent was distilled off, and the residue was purified by silica gel column chromatography to obtain 9.00 g of a white solid. With respect to the obtained product, $^1$H-NMR, IR and Mass spectrum analyses and elemental analysis were conducted to confirm that it was desired 4-(4'-cyanobiphenyl) p-allyloxybenzoate. (yield: 92.1%).

$^1$H-NMR spectrum, δ (CDCl$_3$, ppm): 4.65 (dt, 2H, CH$_2$=CHCH$_2$O—), 5.35 (dd, 1H, CH$_2$=CHCH$_2$O—), 5.45 (dd, 1H, CH$_2$=CHCH$_2$O—), 5.85–6.30 (m, 1H, CH$_2$=CHCH$_2$O—), 7.01 (d, 2H, proton peak of a phenylene group), 7.32 (d, 2H, proton peak of a phenylene group), 7.64 (d, 2H, proton peak of a phenylene group), 7.71 (d, 4H, proton peak of a phenylene group), 8.17 (d, 2H, proton peak of a phenylene group).

IR spectrum (cm$^{-1}$): 2960, 2240 (characteristic absorption by a C—N bond), 1725 (characteristic absorption by a carbonyl group), 1600 (characteristic absorption by a phenylene group), 1580, 1510, 1500, 1420, 1320, 1260, 1210, 1170, 1070, 1000, 950, 825, 765.

Mass spectrum (m/e): 355 (M$^+$), 161, 41 (CH$_2$=CHCH$_2$$^+$).

Elemental analysis (%): Found: C: 77.69, H: 4.79, N: 3.91. Calculated: C: 77.73, H: 7.82, N: 3.94.

2.00 g (5.63 mmol) of 4-(4'-cyanobiphenyl) p-atlyloxybenzoate thus obtained and 3.0 mq (21.8 mmol) of dimethylethoxysilane were dissolved in 60 ml of tetrahydrofuran, and 0.20 ml of a methylene chloride solution of dicyclopentadienylplatinum dichloride (0.1 mol/l) was added thereto. The mixture was stirred at 50° C. for 3 hours under an argon gas atmosphere. The solvent was distilled off to obtain desired 4-(4'-cyanobiphenyl) p-(3-dimethylethoxysilylpropoxy)benzoate as a crude product. Its structure was confirmed by 1H-NMR, but it was an unstable compound and therefore was used to the next reaction as it was.

$^1$H-NMR spectrum, δ (CDCl$_3$, ppm): 0.15 (s, 6H, Si—CH$_3$), 0.64–0.93 (m, 2H, Si—CH$_2$CH$_2$CH$_2$—O), 1.20 ( t, 3H, Si—OCH$_2$CH$_3$), 1.68–2.00 (m, 2H, Si—CH$_2$CH$_2$CH$_2$—O), 3.70 (q, 2H, Si—OCH$_2$CH$_3$), 3.95 (t, 2H, Si—CH$_2$CH$_2$CH$_2$—O), 7.00 (d, 2H, proton peak of a phenylene group), 7.32 (d, 2H, proton peak of a phenylene group), 7.61–7.76 (M, 6H, proton peak of a phenylene group), 8.17 (d, 2H, proton peak of a phenylene group).

2.10 g of the crude product thus obtained was dissolved in 20 mg of acetone and 30 mg of tetrahydrofuran. This solution was poured at room temperature into a solution prepared by dissolving 3.5 g (25.3 mmol) of potassium carbonate in 20 ml of water and 60 ml of acetone. To this solution, an aqueous solution prepared by dissolving 3.5 g (25.3 mmol) of potassium carbonate in 70 ml of water, was further added. The mixture was stirred at room temperature for 2 hours, and then this reaction mixture was poured into an excess amount of ice water containing 8.0 g of potassium dihydrogen phosphate and extracted with methylene chloride. Then, the organic layer was dried over anhydrous sodium sulfate. The solvent was distilled off, and the residue was purified by silica gel column chromatography to obtain 1.35 g of a white solid. With respect to the obtained product, $^1$H-NMR, IR and Mass spectrum analyses and elemental analysis were conducted to confirm that it was desired 4-(4'-cyanobiphenyl) p-(3-dimethylhydroxysilylpropoxy)benzoate. (yield: 55.5% by the two steps).

$^1$H-NMR spectrum, δ (CDCl$_3$, ppm): 1.09 (s, 6H, Si—CH$_3$), 0.67–0.86 (m, 2H, Si—ch2ch2ch2—o), 1.65 (s, 1H, Si—OH), 1.84–1.94 (m, 2H, Si—CH$_2$CH$_2$CH$_2$—O), 4.06 (t, 2H, Si—CH$_2$CH$_2$CH$_2$—O), 7.00 (d, 2H, proton peak of a phenylene group), 7.32 (d, 2H, proton peak of a phenylene group), 7.60–7.77 (m, 6H, proton peak of a phenylene group), 8.16 (d, 2H, proton peak of a phenylene group).

IR spectrum (cm$^{-1}$): 3350 (characteristic absorption by a hydroxyl group), 2970, 2900, 2240 (characteristic absorption by a C—N bond), 1730 (characteristic absorption by a carbonyl group), 1610 (characteristic absorption by a phenylene group), 1510, 1270 (characteristic absorption by a Si—C bond), 1215, 1175, 1080, 1005, 900, 880, 850, 810.

Mass spectrum (m/e): 431 (M$^+$), 416 (M$^+$—Me), 237, 195, 121, 75 (HOMe$_2$Si$^+$)

Elemental analysis (%): Found: C: 69.46, H: 5.69, N: 3.38. Calculated: C: 69.58, H: 5.84, N: 3.25.

EXAMPLE 15

Synthesis 6 of a monomer

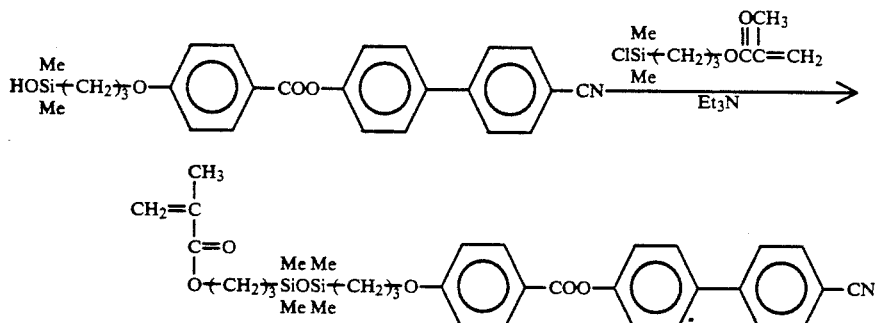

2.70 g (6.26 mmol) of 4-(4'-cyanobiphenyl) p-(3-dimethylhydroxysilylpropoxy)benzoate obtained in Example 14 was dissolved in 10 ml of tetrahydrofuran under an argon gas atmosphere. To this solution, 1.30 ml (9.32 mmol) of triethylamine and 1.8 g (8.16 mmol) of 3-methacryloxypropyldimethylchlorosilane were added, and the mixture was stirred overnight at room temperature. A white salt formed was filtered off while washing it with diethyl ether. The solvent was distilled off, and the residue was purified by silica gel column chromatography to obtain 3.10 g of a white solid. With respect to the obtained product, $^1$H-NMR, IR and Mass spectrum analyses and elemental analysis were conducted to confirm that it was a monomer having the above structure. (yield: 80.4%)

$^1$H-NMR spectrum, δ (CDCl$_3$, ppm): 0.10 ( s, 12H, Si—CH$_3$), 0.48–0.80 (m, 4H, Si—CH$_2$CH$_2$CH$_2$—O×2), 1.59–1.90 (m, 4H, Si—CH$_2$CH$_2$CH$_2$—O ×2), 1.97 (dd, 3H, CH$_2$=C(CH$_3$)COO—), 4.00 (t, 2H, Si—CH$_2$CH$_2$C H$_2$—O), 4.09 (t, 2H, Si—CH$_2$CH$_2$CH$_2$—O), 5.57 (m, 1H, CH$_2$=C(CH$_3$)COO—), 6.13 (m, 1H, CH$_2$=C(CH$_3$)COO—), 7.00 (d, 2H, proton peak of a phenylene group), 7.32 (d, 2H, proton peak of a phenylene group), 7.60–7.77 (m, 6H, proton peak of a phenylene group), 8.16 (d, 2H, proton peak of a phenylene group).

IR spectrum (cm$^{-1}$): 2970, 2900, 2240 (characteristic absorption by C—N bond), 1730 (characteristic absorption by a carbonyl group), 1625, 1610 (characteristic absorption by a phenylene group), 1510, 1260 (characteristic absorption by a Si—C bond), 1170, 1080, 1060 (characteristic absorption by a siloxane bond), 850, 800.

Mass spectrum (m/e): 600 (M$^+$−Me), 516, 421, 217, 121, 69 (CH$_2$=C(CH$_3$) COO$^+$), 41 (CH$_2$=C(CH$_3$)$^+$).

Elemental analysis ( % ): Found: C: 66.36, H: 6.79, N: 2.29. Calculated: C: 66.31, H: 6.71, N: 2.27.

EXAMPLE 16

Synthesis 6 of a polymer

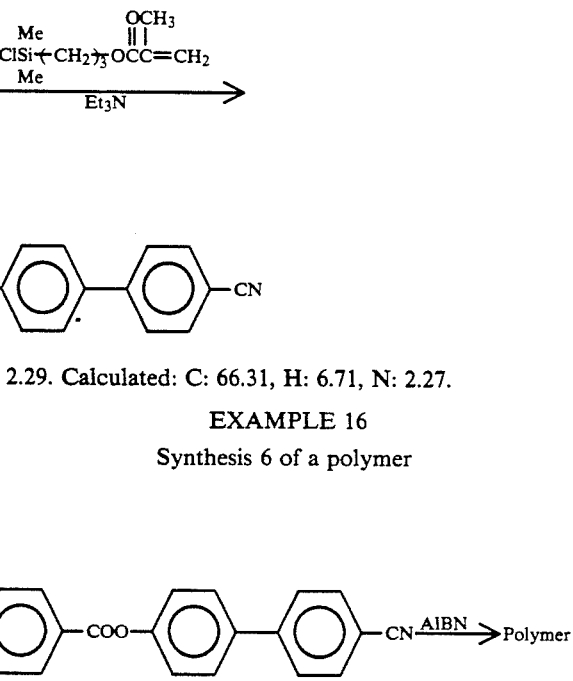

Using 0.50 g (0.35 mmol) of the monomer obtained in Example 15, the polymerization reaction and purification were conducted in the same manner as in Example 3 to obtain 0.35 g of a white solid polymer (yield: 70.0%). With respect to the obtained polymer, $^1$H-NMR and IR spectrum analyses and elemental analysis were conducted to confirm that it was a polymer wherein the repeating units were represented by the formula:

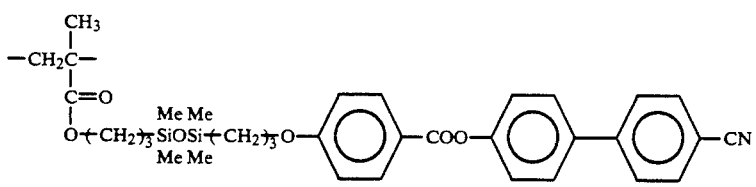

The number average molecular weight and the weight average molecular weight obtained by gel permeation chromatography were 2.08×10$^4$ and 3.68×10$^4$, respectively, as polystyrene standards. The glass transition temperature of this polymer was 22° C. From the DSC measurement and the polarizing microscopic observation, this polymer was found to show smectic liquid crystal phase in a wide temperature range of from 28° C. to 230° C.

$^1$H-NMR spectrum, δ (CDCl$_3$, ppm): 0.10 (s, 12H, Si-CH$_3$), 0.45–0.70 (m, 4H, Si—CH$_2$CH$_2$CH$_2$—O×2), 0.75–1.10 (m, 3H, —CH$_2$C(CH$_3$)—), 1.48–2.00 (m, 6H, Si—CH$_2$CH$_2$CH$_2$—O ×2, —CH$_2$C(CH$_3$)—), 3.92 (m, 4H, Si—CH$_2$CH$_2$CH$_2$—O ×2), 7.00 (d, 2H, proton peak of a phenylene group), 7.32 (d, 2H, proton peak of a phenylene group), 7.60–7.77 (m, 6H, proton peak of a phenylene group), 8.16 (d, 2H, proton peak of a phenylene group).

IR spectrum (cm$^{-1}$): 2970, 2900, 2240 (characteristic absorption by a C—N bond), 1730 (characteristic absorption by a carbonyl group), 1610 (characteristic absorption by a phenylene group), 1510, 1260 (characteristic absorption by a Si—C bond), 1170, 1080, 1060 (characteristic absorption by a siloxane bond), 850, 800.

Elemental analysis (%): Found: C: 66.13; H: 6.73, N: 2.22. Calculated: C: 66.31, H: 6.71, N: 2.27.

EXAMPLE 17

Synthesis 7 of a polymer

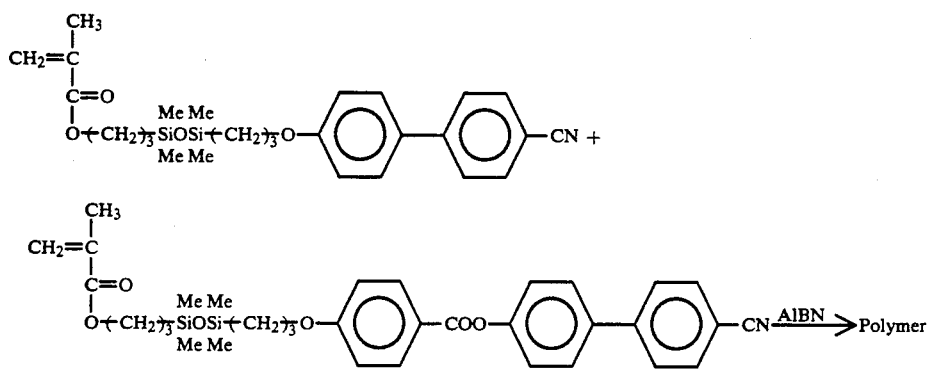

Using 0.40 g (0.76 mmol) of the monomer obtained in Example 2 and 0.47 g (0.76 mmol) of the monomer obtained in Example 15, the polymerization reaction and purification were conducted in the same manner as in Example 3 to obtain 0.37 g of a white solid polymer (yield: 42.5%). With respect to the obtained polymer, $^1$H-NMR and IR spectrum analyses and elemental analysis were conducted to confirm that it was a copolymer wherein the repeating units were represented by the formulas:

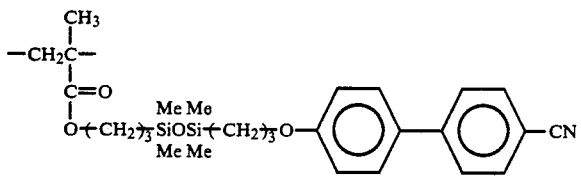

and

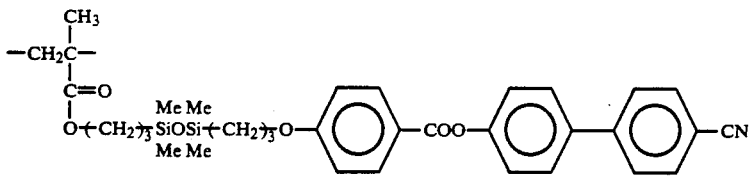

Here, the molar ratio of the repeating units of the former to the repeating units of the latter was found to be 48/52 (mol%) from the $^1$H-NMR spectrum and the results of the elemental analysis. The number average molecular weight and the weight average molecular weight obtained by gel permeation chromatography were 1.06×10$^4$ and 1.78×10$^4$, respectively, as polystyrene standards. The glass transition temperature of this polymer was 9° C.

$^1$H-NMR spectrum, δ (CDCl$_3$, ppm): 0.10 (s, Si—CH$_3$), 0.45–0.70 (m, Si—CH$_2$CH$_2$CH$_2$—O), 0.75–1.10 (m, —CH$_2$C(CH$_3$)—), 1.45–2.00 (m, Si—CH$_2$CH$_2$C-H$_2$—O, —CH$_2$C(CH$_3$)—), 3.65–4.00 (m, Si—CH$_2$CH$_2$CH$_2$—O), 7.00 (d, proton peak of a phenylene group), 7.32 (d, proton peak of a phenylene group), 7.60–7.80 (m, proton peak of a phenylene group), 8.16 (d, 2H, proton peak of a phenylene group).

IR spectrum (cm$^{-1}$): 2970, 2900, 2240 (characteristic absorption by a C—N bond), 1730 (characteristic absorption by a carbonyl group), 1610 (characteristic absorption by a phenylene group), 1510, 1260 (characteristic absorption by a Si—C bond), 1170, 1080, 1060 (characteristic absorption by a siloxane bond), 850, 800.

Elemental analysis (%): Found: C: 65.88, H: 7.31, N: 2.51.

EXAMPLE 18

Synthesis 8 of a polymer

Using 0.40 g (0.76 mmol) of the monomer obtained in Example 2 and 1.41 g (2.29 mmol) of the monomer obtained in Example 15, the polymerization reaction and purification were conducted in the same manner as in Example 3 to obtain 0.58 g of a white solid polymer (yield: 32.0%). With respect to the obtained polymer, $^1$H-NMR and IR spectrum analyses and elemental analysis were conducted to confirm that it was a copolymer having repeating units similar to those of the polymer obtained in Example 17. Here, the molar ratio of the repeating units of the former to the repeating units of the latter as specified in Example 17 was 33/67 (mol%) from the $^1$H-NMR spectrum and the results of the elemental analysis. The $^1$H-NMR and IR spectra were substantially the same as in example 17 except that the peak intensity attributable to the phenylene group in the $^1$H-NMR spectrum was different. The number average molecular weight and the weight average molecular weight obtained by gel permeation chromatography were $7.15 \times 10^4$ and $1.47 \times 10^5$, respectively, as polystyrene standards. The glass transition temperature of this polymer was 16° C. Further, from the DSC measurement and the polarizing microscopic observation, this polymer was found to show a nematic liquid crystal phase within a wide temperature range of from 45° C. to 148° C.

Elemental analysis (%): Found: C: 66.05, H: 7.19, N: 2.43.

EXAMPLE 19

Synthesis 9 of a polymer

Using 0.10 g (0.19 mmol) of the monomer obtained in Example 2 and 2.22 g (3.61 mmol) of the monomer obtained in Example 15, the polymerization reaction and purification were conducted in the same manner as in Example 3 to obtain 1.29 g of a white solid polymer (yield: 55.6%). With respect to the obtained polymer, $^1$H-NMR and IR spectrum analyses and elemental analysis were conducted to confirm that it was a copolymer wherein the repeating units were the same as in the polymer obtained in Example 17. Here, the molar ratio of the repeating units of the former to the repeating units of the latter as specified in Example 17 was 4/96 (mol%) from the $^1$H-NMR spectrum and the results of the elemental analysis. The $^1$H-NMR and IR spectra were substantially the same as in Example 17 except that the peak intensity attributable to the phenylene group in the $^1$H-NMR spectrum was different. The number average molecular weight and the weight average molecular weight obtained by gel permeation chromatography were $1.40 \times 10^4$ and $2.40 \times 10^4$, respectively, as polystyrene standards. The glass transition temperature of this polymer was 18° C. Further, from the DSC measurement and the polarizing microscopic observation, this polymer was found to show a nematic liquid crystal phase within a wide range of from 25° C. to 170° C.

Elemental analysis (%): Found: C: 66.28, H: 6.88, N: 2.30.

EXAMPLE 20

Synthesis 5 of a silanol group having a mesogenic group

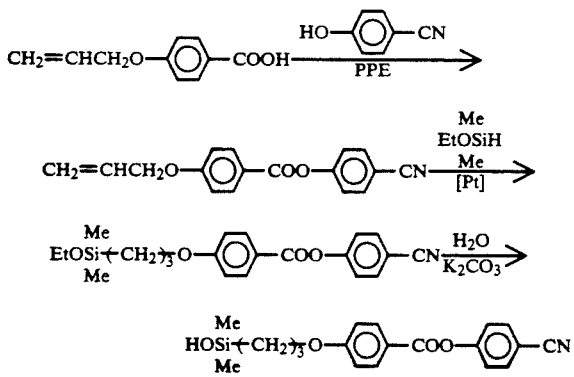

15.0 g of PPE, 4.00 g (22.4 mmol) of p-allyloxybenzoic acid and 2.66 g (22.3 mmol) of p-cyanophenol were dissolved in 100 ml of chloroform under an argon gas atmosphere, and the solution was stirred overnight at room temperature. Water was added thereto, and the mixture was extracted with methylene chloride. The organic layer was dried over anhydrous sodium sulfate. The solvent was distilled off, and the residue was purified by silica gal column chromatography to obtain 4.80 g of a white solid. With respect to the obtained product, $^1$H-NMR, IR and Mass spectrum analyses were conducted to confirm that it was desired p-cyanophenyl p-allyloxybenzoate. (yield: 76.7%).

$^1$H-NMR spectrum, δ (CDCl$_3$, ppm): 4.63 (dt, 2H, CH$_2$=CHC$\underline{H}_2$O—), 5.36 (dd, 1H, C$\underline{H}_2$=CHCH$_2$O—), 5.45 (dd, 1H, C$\underline{H}_2$=CHCH$_2$O—), 5.88–6.24 (m, 1H, CH$_2$=C$\underline{H}$CH$_2$O—), 7.01 (d, 2H, proton peak of a phenylene group), 7.34 (d, 2H, proton peak of a phenylene group), 7.73 (m, 2H, proton peak of a phenylene group), 8.13 (d, 2H, proton peak of a phenylene group).

IR spectrum (cm$^{-1}$): 2960, 2230 (characteristic absorption by a C—N bond), 1720 (characteristic absorption by a carbonyl group), 1600 (characteristic absorption by a phenylene group), 1580, 1500, 1450, 1420, 1325, 1310, 1260, 1200, 1180, 1060, 990, 920, 880, 840, 755.

Mass spectrum (m/e): 279 (M$^+$), 161, 41 (CH$_2$=CHCH$_2$$^+$). 1.90 g (5.72 mmol) of p-cyanophenyl p-allyloxybenzoate thus obtained and 2.50 ml (18.2 mmol) of dimethylethoxysilane were dissolved in 30 ml of tetrahydrofuran, and 0.20 ml of a methylene chloride solution of dicyclopentadienylplatinum dichloride (0.1 mol/l) was added thereto. The mixture was stirred at 50° C. for 3 hours under an argon gas atmosphere. The solvent was distilled off, and the residue was purified by silica gal column chromatography to obtain 1.80 g of a colorless transparent liquid. With respect to the obtained product, $^1$H-NMR IR and Mass spectrum analyses, were conducted to confirm it was desired p-cyanophenyl p-(3-dimethylethoxysilylpropoxy)benzoate. (yield: 72.9%).

$^1$H-NMR spectrum, δ (CDCl$_3$, ppm): 4.63 (dt, 2H, CH$_2$=CHC$\underline{H}_2$O—) , 5.36 (dd, $^1$H, C$\underline{H}_2$=CHCH$_2$O—), 5.45 (dd, $^1$H, C$\underline{H}_2$=CHCH$_2$O—), 5.88–6.24 (m, $^1$H, CH$_2$=C$\underline{H}$CH$_2$O—), 7.01 (d, 2H, proton peak of a phenylene group), 7.34 (d, 2H, proton peak of a phenylene group), 7.73 (d, 2H, proton peak of a phenylene group), 8.13 (d, 2H, proton peak of a phenylene group).

IR spectrum (cm$^{-1}$): 2960, 2230 (characteristic absorption by a C—N bond), 1720 (characteristic absorption by a carbonyl group), 1600 (characteristic absorption by a phenylene group), 1580, 1500, 1450, 1420, 1325, 1310, 1260, 1200, 1180, 1060, 990, 920, 880, 840, 755.

Mass spectrum (m/e): 279 (M$^+$), 161, 41 (CH$_2$=CHCH$_2$$^+$). 1.75 g of p-cyanophenyl p-(3-dimethylethoxysilylpropoxy)benzoate thus obtained, was dissolved in 35 ml of acetone. This solution was poured at room temperature into a solution prepared by dissolving 1.5 g (10.9 mmol) of potassium carbonate in 25 ml of water and 60 ml of acetone. Further, to this solution, an aqueous solution prepared by dissolving 1.5 g (10.9 mmol) of potassium carbonate in 45 ml of water, was added. The mixture was stirred at room temperature for 2 hours. Then, this reaction mixture was poured into an excess amount of ice water containing 5.0 g of potassium dihydrogen phosphate and extracted with methylene chloride. Then, the organic layer was dried over anhydrous sodium sulfate. The solvent was distilled off, and the residue was purified by silica gel column chromatography to obtain 1.40 g of a white solid. With respect to the obtained product, $^1$H-NMR IR and Mass spectrum analyses were conducted to confirm that it was desired p-cyanophenyl p-(3-dimethylhydroxysilylpropoxy)benzoate. (yield: 86.4%)

1H-NMR spectrum, δ (CDCl3, ppm): 0.19 (s, 6H, Si—CH3), 0.67–0.89 I(m, 2H, Si—CH2CH2CH2—O), 1.70 (s, 1H, Si—OH), 1.83–2.02 (m, 2H, Si—CH2CH2CH2—O), 3.67 (t, 2H, Si—CH 2CH2CH2—O), 6.98 (d, 2H, proton peak of a phenylene group), 7.35 (d, 2H, proton peak of a phenylene group), 7.73 (d, 2H, proton peak of a phenylene group), 8.12 (d, 2H, proton peak of a phenylene group)

IR spectrum (cm⁻¹): 3500 (characteristic absorption by a hydroxyl group), 2950, 2880, 2240 (characteristic absorption by a C—N bond), 1930, 1720 (characteristic absorption by a carbonyl group), 1600 (characteristic absorption by a phenylene group), 1510, 1470, 1410, 1390, 1320, 1250 (characteristic absorption by a Si—C bond), 1200, 1150, 1040, 1000, 870, 820, 760.

Mass spectrum (m/e): 355 (M+), 340 (M+−Me), 237, 195, 121, 75 (HOMe2Si+).

EXAMPLE 21

Synthesis 7 of a monomer

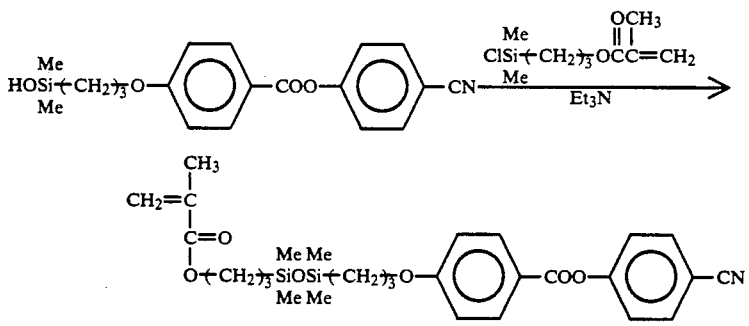

1.25 g (3.52 mmol) of p-cyanophenyl p-(3-dimethylhydroxysilylpropoxy)benzoate obtained in Example 20 was dissolved in 15 ml of tetrahydrofuran under an argon gas atmosphere. To this solution, 1.00 ml (7.17 mmol) of triethylamine and 0.93 g (4.22 mmol) of 3-methacryloyloxypropyldimethylchlorosilane were added, and the mixture was stirred overnight at room temperature. A white salt formed was filtered off while washing it with diethyl ether. The solvent was distilled off, and the residue was purified by silica gel column chromatography to obtain 1.72 g of a white solid. With respect to the obtained product, 1H-NMR IR and Mass spectrum analyses , were conducted to confirm that it was a monomer having the above structure. (yield: 90.5%).

1H-NMR spectrum, δ (CDCl3, ppm): 0.10 (s, 12H, Si—CH3), 0.53–0.75 (m, 4H, Si—CH2CH2CH2—O×2), 1.61–1.96 (m, 4H, Si—CH2CH2CH2—O ×2), 1.94 (dd, 3H, CH2=C(CH3)COO—), 4.03 (t, 2H, Si—CH2CH2CH2—O), 4.31 (t, 2H, Si—CH2CH2CH2—O), 5.53 (m, 1H, CH2=C(CH3)COO—), 6.10 (m, 1H, CH2=C(CH3)COO—), 6.98 (d, 2H, proton peak of a phenylene group), 7.35 (d, 2H, proton peak of a phenylene group), 7.73 (d, 2H, proton peak of a phenylene group), 8.12 (d, 2H, proton peak of a phenylene group).

IR spectrum (cm⁻¹): 2950, 2900, 2250 (characteristic absorption by a C—N bond), 1740 (characteristic absorption by a carbonyl group), 1720, 1600 (characteristic absorption by a phenylene group), 1510, 1320, 1300, 1255 (characteristic absorption by a Si—C bond), 1210, 1160, 1060 (characteristic absorption by a siloxane bond), 1000, 840, 800.

Mass spectrum (m/e): 524 (M+−Me), 482, 440, 421, 217, 121, 69 (CH2=C(CH3)COO+), 41 (CH2=C(CH3)+).

EXAMPLE 22

Synthesis 10 of a polymer

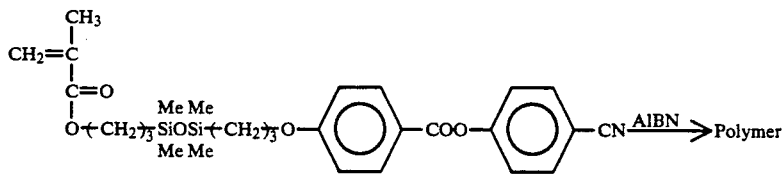

Using 1.49 g (2.76 mmol) of the monomer obtained in Example 21, the polymerization reaction and purification were conducted in the same manner as in Example 3 to obtain 1.10 g of a white solid polymer (yield: 73.8%). With respect to the obtained polymer, 1H-NMR and IR spectrum analyses and elemental analysis were conducted to confirm that it was a polymer wherein the repeating units were represented by the formula:

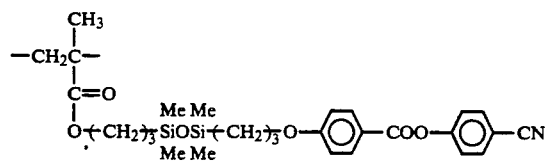

The number average molecular weight and the weight average molecular weight obtained by gel permeation chromatography were 3.49×10⁴ and 6.40×10⁴, respectively, as polystyrene standards. The glass transition temperature of this polymer was 7° C.

1H-NMR spectrum, δ (CDCl3, ppm): 0.08 (s, 12H, Si—CH3), 0.39–0.55 (m, 4H, Si—CH2CH2CH2—O×2), 0.70–1.20 (m, 3H, —CH2C(CH3)—), 1.38–1.84 (m, 6H, Si—CH2CH2CH2—O×2, -CH2C(CH3)—), 3.94 (m, 4H, Si—CH2CH2CH2—O×2), 6.93 (d, 2H, proton peak of a phenylene group), 7.30 (d, 2H, proton peak of a phenylene group), 7.67 (d, 2H, proton peak of a phenylene group), 8.07 (d, 2H, proton peak of a phenylene group).

IR spectrum (cm$^{-1}$): 3010, 2950, 2880, 2210 (characteristic absorption by a C—N bond), 1725 (characteristic absorption by a carbonyl group), 1600 (characteristic absorption by a phenylene group), 1510, 1250 (characteristic absorption by a Si—C bond), 1200, 1160, 1055 (characteristic absorption by a siloxane bond), 1000, 840, 790.

Elemental analysis (%): Found: C: 62.24, H: 7.10, N: 2.38. Calculated: C: 62.31, H: 6.91, N: 2.59.

EXAMPLE 23

Synthesis 6 of a silanol compound having a mesogenic group 1470, 1450, 1420, 1390, 1315, 1300, 1270, 1250, 1190 1160, 1070, 1000, 985, 920, 870, 840, 800, 770.

Mass spectrum (m/e): 354 (M+), 116, 41 (CH$_2$=CHCH$_2$+).

4.00 g (11.3 mmol) of p-hexyloxyphenyl p-allyloxybenzoate thus obtained and 3.0 ml (21.8 mmol) of dimethylethoxysilane were dissolved in 50 ml of tetrahydrofuran, and 0.20 ml of a methylene chloride solution of dicyclopentadienylplatinum dichloride (0.1 mol/l) was added thereto. The mixture was stirred at 50° C. for 3 hours under an argon gas atmosphere. The solvent was distilled off to obtain desired p-hexyloxyphenyl p-(3-dimethylethoxysilylpropoxy)benzoate as a crude product.

The crude product thus obtained was dissolved in 70 ml of acetone. This solution was poured at room temperature into a solution prepared by dissolving 3.0 g

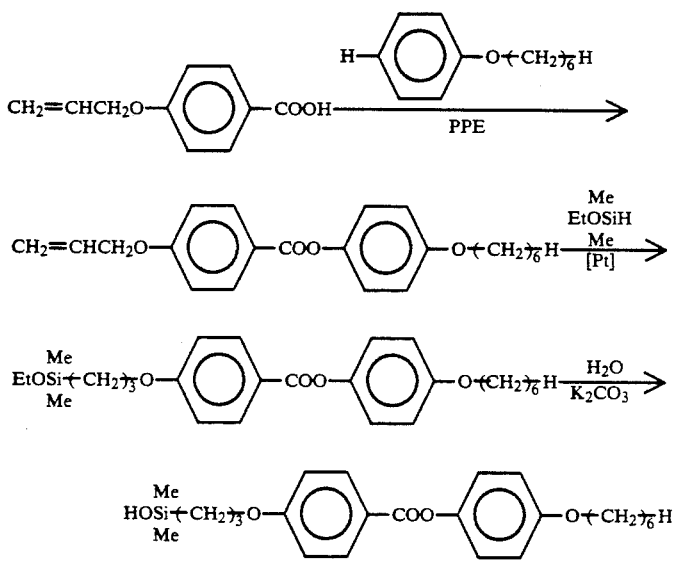

15.0 g of PPE, 4.00 g (22.4 mmol) of p-allyloxybenzoic acid and 4.40 g (22.6 mol) of p-hexyloxyphenol were dissolved in 100 mg of chloroform under an argon gas atmosphere, and the solution was stirred overnight at room temperature. Water was added thereto, and the mixture was extracted with methylene chloride. The organic layer was dried over anhydrous sodium sulfate. The solvent was distilled off, and the residue was purified by silica gel colum chromatography to obtain 6.10 g of a white solid. With respect to the obtained product, $^1$H-NMR, IR and Mass spectrum analyses were conducted to confirm that it was desired p-hexyloxyphenyl p-allyloxybenzoate. (yield: 76.8%).

$^1$H-NMR spectrum, δ (CDCl$_3$, ppm): 0.92 (t, 3H, —OCH$_2$(CH$_2$)$_4$CH$_3$), 1.23–1.83 (m, 8H, —OCH$_2$(CH$_2$)$_4$CH$_3$), 3.96 (5, 2H, —OCH$_2$(CH$_2$)$_4$CH$_3$), 4.63 (dt, 2H, CH$_2$=CHCH$_2$O—), 5.35 (dd, 1H, CH$_2$=CHCH$_2$O—), 5.43 (dd, 1H, CH$_2$=CHCH$_2$O—), 5.90–6.25 (m, 1H, CH$_2$=CHCH$_2$O—), 6.90 (d, 2H, proton peak of a phenylene group), 6.98 (d, 2H, proton peak of a phenylene group), 7.10 (d, 2H, proton peak of a phenylene group), 8.13 (d, 2H, proton peak of a phenylene group).

IR spectrum (cm$^{-1}$): 2960, 2940, 2860, 1720 (characteristic absorption by a carbonyl group), 1600 (characteristic absorption by a phenylene group), 1580, 1610, (21.7 mmol) of potassium carbonate in 50 ml of water and 100 ml of acetone. To this solution, an aqueous solution prepared by dissolving 3.0 g (21.7 mmol) of potassium carbonate in 80 ml of water, was added. The mixture was stirred at room temperature for 4 hours. Then, this reaction mixture was poured into an excess amount of ice water containing 8.0 g of potassium dihydrogen phosphate and extracted with methylene chloride. Then, the organic layer was dried over anhydrous sodium sulfate. The solvent was distilled off, and the residue was purified by silica gel column chromatography to obtain 2.81 g of a white solid. With respect to the obtained product, $^1$H-NMR, IR and Mass spectrum analyses were conducted to confirm that it was desired p-hexyloxyphenyl p-(3-dimethylhydroxysilylpropoxy)-benzoate. (yield: 57.7% by two stages).

$^1$H-NMR spectrum, δ (CDCl$_3$, ppm): 0.19 (s, 6H, Si—CH$_3$), 0.66–0.76 (m, 2H, Si—CH$_2$CH$_2$CH$_2$—O), 0.93 (t, 3H, —OCH$_2$(CH$_2$)$_4$CH$_3$), 1.22–2.06 (m, 11H, —OCH$_2$(CH$_2$)$_4$CH$_3$, Si—OH, Si—CH$_2$CH$_2$CH$_2$—O), 3.96 (t, 2H, —OCH$_2$(CH$_2$)$_4$CH$_3$), 4.04 (t, 2H, Si—CH$_2$CH$_2$CH$_2$—O), 6.90 (d, 2H, proton peak of a phenylene group), 6.96 (d, 2H, proton peak of a phenylene group), 7.11 (d, 2H, proton peak of a phenylene group), 8.13 (d, 2H, proton peak of a phenylene group).

IR spectrum (cm$^{-1}$): 3250 (characteristic absorption by a hydroxyl group), 2590, 2880, 1720 (characteristic absorption by a carbonyl group), 1600 (characteristic absorption by a phenylene group), 1500, 1470, 1420, 1380, 1310, 1280 (characteristic absorption by a Si—C bond), 1220, 1180, 1160, 1070 1030, 1000, 880, 840, 810, 760.

Mass spectrum (m/e): 430 (M+), 237, 195, 121, 75 (HOMe$_2$Si+).

EXAMPLE 24

Synthesis 8 of a monomer

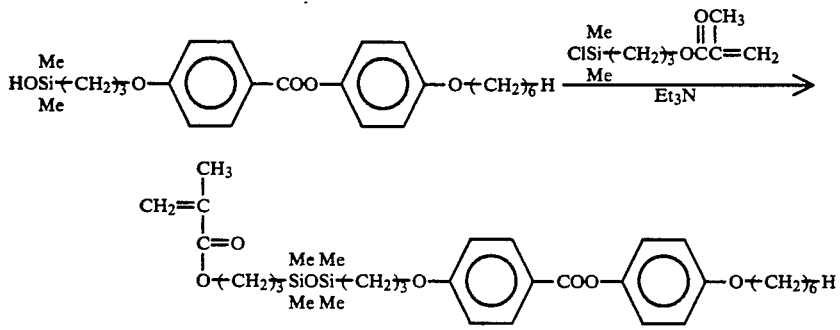

2.20 g (5.11 mmol) of p-hexyloxyphenyl p-(3-dimethylhydroxysilylpropoxy)benzoate obtained in Example 23 was dissolved in 20 ml of tetrahydrofuran under an argon atmosphere. To this solution, 1.40 ml (10.0 mmol) of triethylamine and 1.30 g (5.89 mmol) of 3-methacryloxypropyldimethylchlorosilane were added, and the mixture was stirred overnight at room temperature. A white salt formed was filtered off while washing it with diethyl ether. The solvent was distilled off, and the residue was purified by silica gel column chromatography to obtain 2.8 g of a white solid. With respect to the obtained product, $^1$H-NMR IR and Mass spectrum analyses were conducted to confirm that it was a monomer having the above structure. (yield: 89.1%).

$^1$H-NMR spectrum, δ (CDCl$_3$, ppm): 1.10 (s, 12H, Si—CH$_3$), 0.47–0.75 (m, 4H, Si—CH$_2$CH$_2$CH$_2$—O×2), 0.91 (t, 3H, —OCH$_2$(CH$_2$)$_4$CH$_3$), 1.25–1.90 (m, 12H, Si—CH$_2$CH$_2$CH$_2$—O×2, —OCH$_2$(CH$_2$)$_4$CH$_3$), 1.95 (dd, 3H, CH$_2$=C(CH$_3$)COO—), 3.96 (t, 2H, —OCH$_2$(CH$_2$)$_4$CH$_3$), 4.01 (t, 2H, Si—CH$_2$CH$_2$CH$_2$—O), 4.11 (t, 2H, Si—CH$_2$CH$_2$CH$_2$—O), 5.54 (m, 1H, CH$_2$=C(CH$_3$)COO—), 6.10 (m, 1H, CH$_2$=C(CH$_3$)COO—), 6.90 (d, 2H, proton peak of a phenylene group), 6.96 (d, 2H, proton peak of a phenylene group), 7.11 (d, 2H, proton peak of a phenylene group), 8.13 (d, 2H, proton peak of a phenylene group)

IR spectrum (cm$^{-1}$): 2950, 2870, 1720 (characteristic absorption by a carbonyl group), 1610 (characteristic absorption by a phenylene group), 1510, 1250 (characteristic absorption by a Si—C bond), 1190, 1160, 1070, 1050 (characteristic absorption by a siloxane bond), 1000, 840, 800.

Mass spectrum ( m/e ): 614 (M+), 515, 421, 217, 69 (CH$_2$=C(CH$_3$)COO+), 41 (CH$_2$=C( CH$_3$)+).

EXAMPLE 25

Synthesis 1! of a polymer

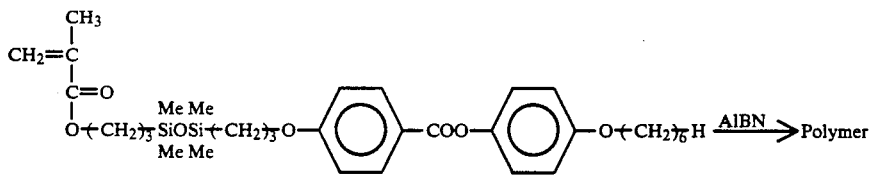

Using 2.00 g (3.25 mmol) of the monomer obtained in Example 24, the polymerization reaction and purification were conducted in the same manner as in Example 3 to obtain 1.20 g of a white solid polymer (yield: 60.0%). With respect to the obtained polymer, $^1$H-NMR and IR spectrum analyses and elemental analysis were conducted to confirm that it was a polymer wherein the repeating units were represented by the formula:

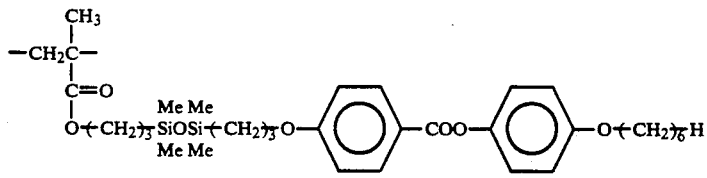

The number average molecular weight and the weight average molecular weight obtained by gel permeation chromatography were 4.69×10$^4$ and 9.28×10$^4$, respectively, as polystyrene standards. The glass transition temperature of this polymer was −1° C.

$^1$H-NMR spectrum, δ (CDCl$_3$, ppm ): 0.08 (s, 12H, Si—CH$_3$), 0.30–0.65 (m, 4H, Si—CH$_2$CH$_2$CH$_2$—O×2), 0.75–1.20 (m, 6H,—CH$_2$C(CH$_3$)—, —OCH$_2$(CH$_2$)$_4$CH$_3$), 1.28–2.00 (m, 14H, Si—CH$_2$CH$_2$CH$_2$—O×2, —CH$_2$C(CH$_3$)—, —OCH$_2$(CH$_2$)$_4$CH$_3$), 3.84–3.97 (m, 6H, Si—CH$_2$CH$_2$CH$_2$—O×2, —OCH$_2$(CH$_2$)$_4$CH$_3$), 6.86 (d, 2H, proton peak of a phenylene group), 6.90 (d, 2H, proton peak of a phenylene group), 7.06 (d, 2H, proton peak of a phenylene group), 8.08 (d, 2H, proton peak of a phenylene group).

IR spectrum (cm$^{-1}$): 2950, 2900, 2850, 1730 (characteristic absorption by a carbonyl group), 1600 (characteristic absorption by a phenylene group), 1575, 1500, 1460, 1415, 1385, 1250 (characteristic absorption by a Si—C bond), 1190, 1160, 1050 (characteristic absorption by a siloxane bond), 1000, 885, 830, 780.

Elemental analysis (%): Found: C: 64.40, H: 8.34. Calculated: C: 64.46, H: 8.20.

EXAMPLE 26 synthesis 7 of a silanol compound having a mesogenic group

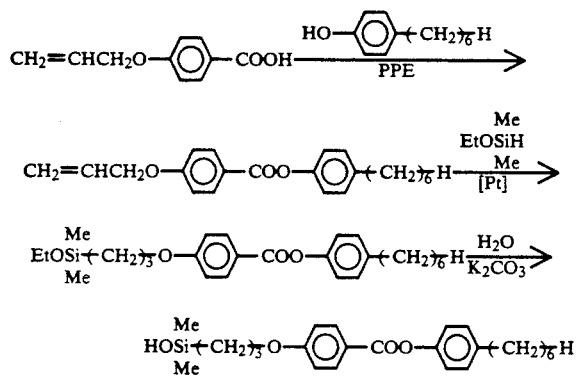

15.0 g of PPE, 4.00 g (22.4 mmol) of p-allyloxybenzoic acid and 4.00 g (22.4 mmol) of p-hexylphenol were dissolved in 100 ml of chloroform under an argon gas atmosphere, and the solution was stirred overnight at room temperature. Water was added to the solution, and the mixture was extracted with methylene chloride. The organic layer was dried over anhydrous sodium sulfate. The solvent was distilled off, and the residue was purified by silica gel column chromatography to obtain 6.50 g of a white solid. With respect to the obtained product, $^1$H-NMR, IR and Mass spectrum analyses were conducted to confirm that it was desired p-hexylphenyl p-allyloxybenzoate. (yield: 85.7%)

$^1$H-NMR spectrum, a (CDCl$_3$, ppm): 0.92 (t, 3H, —CH$_2$(CH$_2$)$_4$CH$_3$), 1.25–1.85 (m, 8H, —OCH$_2$(CH$_2$)$_4$CH$_3$), 2.62 (t, 2H, —OCH—$_2$(CH$_2$)$_4$CH$_3$), 4.62 (dt, 2H, CH$_2$=CHCH$_2$O—), 5.36 (dd, 1H, CH$_2$=CHCH$_2$O—), 5.43 (dd, 1H, CH$_2$=CHCH$_2$O—), 5.88–6.30 (m, 1H, CH$_2$=CHCH$_2$O—), 6.98 (d, 2H, proton peak of a phenylene group), 7.15 (d, 4H, proton peak of a phenylene group), 8.14 (d, 2H, proton peak of a phenylene group).

IR spectrum (cm$^{-1}$): 2960, 2940, 2850, 1720 (characteristic absorption by a carbonyl group), 1610 (characteristic absorption by a phenylene group), 1580, 1510, 1450, 1420, 1410, 1280, 1260, 1200, 1160, 1100, 1070, 1010, 1000, 915, 880, 840, 810, 760.

Mass spectrum (m/e): 338 (M$^+$), 161, 41 (CH$_2$=CHCH$_2$$^+$). 4.00 g (11.8 mmol) of p-hexylphenyl p-allyloxybenzoate thus obtained and 2.50 ml (18.2 mmol) of dimethylethoxysilane were dissolved in 50 ml of tetrahydrofuran, and 0.20 ml of a methylene chloride solution of dicyclopentadienylplatinum dichloride (0.1 mol/l) was added thereto. The mixture was stirred at 50° C. for 3 hours under an argon gas atmosphere. The solvent was distilled off to obtain desired p-hexylphenyl p-(3-dimethyethoxysilylpropoxy)benzoate as a crude product.

The crude product thereby obtained was dissolved in 70 ml of acetone. This solution was poured at room temperature into a solution prepared by dissolving 3.0 g (21.7 mmol) of potassium carbonate in 50 ml of water and 100 ml of acetone. Further, to this solution, an aqueous solution prepared by dissolving 3.0 g (21.7 mmol) of potassium carbonate in 80 ml of water, was further added. The mixture was stirred at room temperature for 2 hours. Then, this reaction mixture was poured into an excess amount of ice water containing 8.0 g of potassium dihydrogen phosphate and extracted with methylene chloride. Then, the organic layer was dried over anhydrous sodium sulfate. The solvent was distilled off, and the residue was purified by silica gel column chromatography to obtain 2.20 g of a white solid. With respect to the obtained product, $^1$H-NMR, IR and Mass spectrum analyses were conducted to confirm that it was desired p-hexylphenyl p-(3-dimethylhydroxysilylpropoxy)benzoate. (yield: 45.0% by two stages).

$^1$H-NMR spectrum, δ (CDCl$_3$, ppm): 0.20 (s, 6H, Si—CH$_3$), 0.67–0.78 (m, 2H, Si—CH$_2$CH$_2$CH$_2$—O), 0.95 (t, 3H, —CH$_2$(CH$_2$)$_4$CH$_3$), 1.22–1.83 (m, 11H, —CH$_2$(CH$_2$)$_4$CH$_3$, Si—OH, Si—CH$_2$CH$_2$CH$_2$—O), 2.64 (t, 2H, —CH$_2$C(CH$_2$)$_4$CH$_3$), 4.05 (t, 2H, Si—CH$_2$CH$_2$CH$_2$—O), 6.97 (d, 2H, proton peak of a phenylene group), 7.16 (d, 4H, proton peak of a phenylene group), 8.15 (d, 2H, proton peak of a phenylene group).

IR spectrum (cm$^{-1}$): 3200 (characteristic absorption by a hydroxyl group), 2960, 2930, 2850, 1720 (characteristic absorption by a carbonyl group), 1600 (characteristic absorption by a phenylene group), 1580, 1510, 1470, 1420, 1260 (characteristic absorption by a Si—C bond), 1200, 1180, 1060, 1040, 1015, 995, 900, 860, 840, 760

Mass spectrum (m/e):
414 (M$^+$), 397 (M$^+$—OH), 237, 195, 121, 75 (HOMe$_2$Si$^+$).

EXAMPLE 27

Synthesis 9 of a monomer

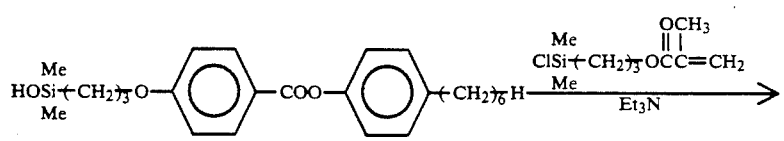

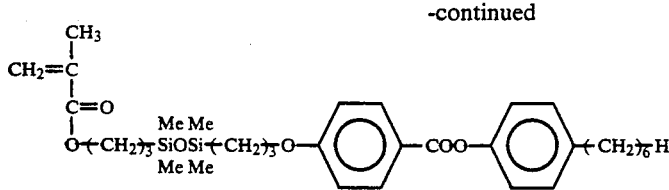

1.65 g (3.98 mmol) of p-hexylphenyl p-(3-dimethylhydroxysilylpropoxy)benzoate obtained in Example 26 was dissolved in 15 ml of tetrahydrofuran under an argon gas atmosphere. To this solution, 1.20 ml (8.62 mmol) of triethylamine and 1.05 g (4.76 mmol) of 3-methacryloxypropyldimethylchlorosilane were added, and the mixture was stirred overnight at room temperature. A white salt formed was filtered off while washing it with diethyl ether. The solvent was distilled off, and the residue was purified by silica gel column chromatography to obtain 2.26 g of a white solid. With respect to the obtained product, $^1$H-NMR, IR and Mass spectrum analyses were conducted to confirm that it was a monomer having the above structure. (yield: 94.8%)

$^1$H-NMR spectrum, δ (CDCl$_3$, ppm): 0.10 (s, 12H, Si—CH$_3$), 0.56–0.75 (ml 4H, Si—$\overline{\text{CH}_2}$CH$_2$CH$_2$—O×2), 0.92 (t, 3H, —CH$_2$(CH$_2$)$_4$$\overline{\text{CH}_3}$), 1.21–1.95 (m, 12H, Si—CH$_2$$\overline{\text{CH}_2}$CH$_2$—O×2, —$\overline{\text{CH}_2}$(CH$_2$)$_4$CH$_3$), 1.94 (dd, 3H, $\overline{\text{CH}_2}$=C(CH$_3$)COO—), 2.58 (t, 2H, —CH$_2$(CH$_2$)$_4$$\overline{\text{CH}_3}$), 4.01 (t, 2H, Si—CH$_2$CH$_2$$\overline{\text{CH}_2}$—O), 4.11 (t, 2H, Si—CH$_2$CH$_2$$\overline{\text{CH}_2}$—O), 5.53 (m, 1H, CH$_2$=C(CH$_3$)COO—), 6.10 (m, 1H, $\overline{\text{CH}_2}$=C(CH$_3$)COO—), 6.90 (d, 2H, proton peak of a phenylene group), 7.20 (d, 4H, proton peak of a phenylene group), 8.13 (d, 2H, proton peak of a phenylene group).

IR spectrum (cm$^{-1}$): 2955, 2590, 2870, 1720 (characteristic absorption by a carbonyl group), 1610 (characteristic absorption by a phenylene group), 1510, 1320, 1300, 1255 (characteristic absorption by a Si—C bond), 1200, 1160, 1070, 1050 (characteristic absorption by a siloxane bond), 1010, 840, 800.

Mass spectrum (m/e): 598 (M+), 583 (M+—Me), 541, 499, 421, 217, 121, 69 (CH$_2$=C(CH$_3$)COO+), 41 (CH$_2$=C(CH$_3$)+),

EXAMPLE 28

Synthesis 12 of a polymer

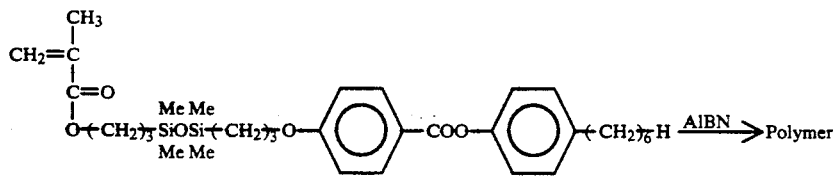

Using 1.60 g (2.67 mmol) of the monomer obtained in Example 27, the polymerization reaction and purification were conducted in the same manner as in Example 3 to obtain 1.10 g of a viscous liquid polymer (yield: 68.8%). With respect to the obtained polymer, $^1$H-NMR and IR spectrum analyses and elemental analysis were conducted to confirm that it was a polymer wherein the repeating units were represented by the formula:

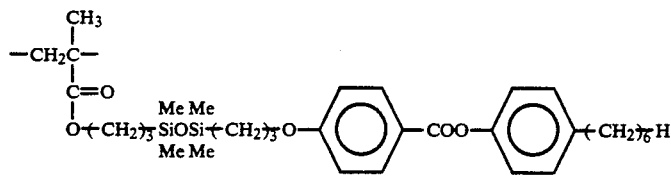

The number average molecular weight and the weight average molecular weight obtained by gel permeation chromatography were 3.52×10$^4$ and 7.19×10$^4$ respectively, as polystyrene standards. The glass transition temperature of this polymer was −18° C.

$^1$H-NMR spectrum, δ (CDCl$_3$, ppm): 0.08 (s, 12H, Si—CH$_3$), 0.40–0.65 (m, 4H, Si—$\overline{\text{CH}_2}$CH$_2$CH2—O×2), 0.75–1.20 (m, 6H, —CH$_2$C(CH$_3$)—, —CH$_2$(CH$_2$)$_4$CH$_3$), 1.25–1.90 (m, 14H, Si—CH$_2$$\overline{\text{CH}_2}$CH$_2$—O ×2,—CH$_2$C(CH$_3$)—, —CH$_2$(CH$_2$)$_4$CH$_3$), 2.54 (t, 2H, —CH$_2$($\overline{\text{CH}_2}$)$_4$CH$_3$), 3.95 (t, 4H, Si—CH$_2$CH$_2$-$\overline{\text{H}_2}$—O×2), 6.90 (d, 2H, proton peak of a phenylene group), 7.10 (d, 4H, proton peak of a phenylene group), 8.10 (d, 2H, proton peak of a phenylene group).

IR spectrum (cm$^{-1}$): 2950, 2930, 2860, 2850, 1730 (characteristic absorption by a carbonyl group), 1605 (characteristic absorption by a phenylene group), 1580, 1510, 1470, 1420, 1315, 1250 (characteristic absorption by a Si—C bond), 1190, 1160, 1060 (characteristic absorption by a siloxane bond), 840, 795, 760, 690.

Elemental analysis (%): Found: C: 66.09, H: 8.56. Calculated: C: 66.18, H: 8.41.

EXAMPLE 29

Synthesis 8 of a silanol compound having a mesogenic group

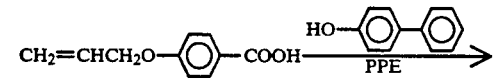

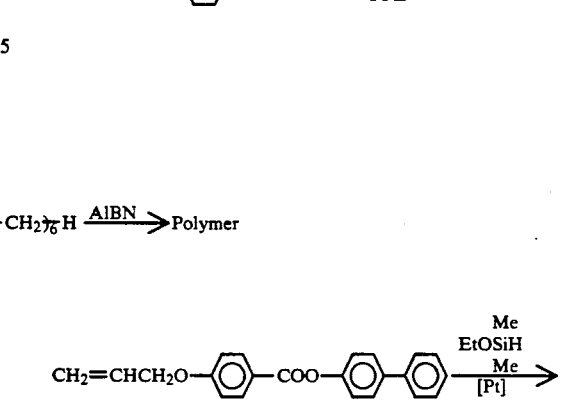

-continued

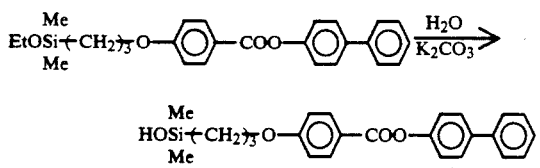

15.0 g of PPE, 3.67 g (20.6 mmol) of p-allyloxybenzoic acid and 3.50 g (20.6 mmol) of p-phenylphenol were dissolved in 100 ml of chloroform under an argon gas atmosphere, and the solution was stirred overnight at room temperature. Water was added to the solution, and the mixture was extracted with methylene chloride. The organic layer was dried over anhydrous sodium sulfate, and the solvent was distilled off. The residue was purified by silica gel column chromatogaphy and further recrystallized from ethyl acetate to obtain 4.45 g of a white solid. With respect to the obtained product, $^1$H-NMR, IR and Mass spectrum analyses were conducted to confirm that it was desired 4-biphenyl p-allyloxybenzoate. (yield: 65.4%).

$^1$H-NMR spectrum, δ (CDCl$_3$, ppm): 4.63 (dr, 2H, CH$_2$=CHCH$_2$O—), 5.35 (dd, 1H, CH$_2$=CHCH$_2$O—), 5.44 (dd, 1H, CH$_2$=CHCH$_2$O—), 5.76-6.24 (m, 1H, CH$_2$=CHCH$_2$O—), 7.01 (d, 2H, proton peak of a phenylene group), 7.22-7.68 (m, 9H, proton peak of a phenylene group), 8.17 (d, 2H, proton peak of a phenylene group).

IR spectrum (cm$^{-1}$): 3070, 2900, 1725 (characteristic absorption by a carbonyl group), 1605 (characteristic absorption by a phenylene group), 1580, 1510, 1485, 1450, 1420, 1405, 1380, 1310, 1250, 1210, 1180, 1160, 1105, 1060, 980, 920, 880, 840, 760, 690.

Mass spectrum (m/e): 330 (M+), 161, 41 (CH$_2$=CHCH$_2$+).

4.10 g (12.4 mmol) of 4-biphenyl p-allyloxybenzoate thus obtained and 2.40 ml (17.4 mmol) of dimethylethoxysilane were dissolved in 50 ml of tetrahydrofuran, and 0.20 ml of a methylene chloride solution of dicyclopentadienylplatinum dichloride (0.1 mol/l) was added thereto. The mixture was stirred at 50° C. for 3 hours under an argon gas atmosphere. The solvent was distilled off to obtain desired 4-biphenyl p-(3-dimethylethoxysilylpropoxy)benzoate as a crude product.

The crude product thereby obtained was dissolved in 100 ml of acetone. This solution was poured at room temperature into a solution prepared by dissolving 2.0 g (14.5 mmol) of potassium carbonate in 40 ml of water and 100 ml of acetone. To this solution, an aqueous solution prepared by dissolving 2.0 g (14.5 mmol) of potassium carbonate in 80 mg of water, was further added. The mixture was stirred at room temperature for 2 hours. Then, this reaction mixture was poured into an excess amount of ice water containing 8.0 g of potassium dihydrogen phosphate and extracted with methylene chloride. Then, the organic layer was dried over anhydrous sodium sulfate. The solvent was distilled off, and the residue was purified by silica gel column chromatography to obtain 2.50 g of a white solid. With respect to the obtained product, $^1$H-NMR IR and Mass spectrum analyses were conducted to confirm that it was desired 4-biphenyl p-(3-dimethylhydroxysilyl propoxy)benzoate. (yield: 49.6% by two stages).

$^1$H-NMR spectrum, δ (CDCl$_3$, ppm): 0.20 (s, 6H, Si—CH$_3$), 0.67-0.86 (m, 2H, Si—CH$_2$CH$_2$CH$_2$—O), 1.64 (s, 1H, Si—OH), 1.74-2.12 (m, 4H, Si—CH$_2$CH$_2$CH$_2$—O), 4.06 (t, 2H, Si—CH$_2$CH$_2$CH$_2$—O), 6.99 (d, 2H, proton peak of a phenylene group), 7.23-7.68 (m, 9H, proton peak of a phenylene group), 8.17 (d, 2H, proton peak of a phenylene group).

IR spectrum (cm$^{-1}$): 3400, 3200 (characteristic absorption by a hydroxyl group), 3060, 2950, 2850, 1720 (characteristic absorption by a carbonyl group), 1700, 1600 (characteristic absorption by a phenylene group), 1580, 1510, 1485, 1420, 1320, 1260 (characteristic absorption by a Si—C bond), 1220, 1160, 1070, 1000, 880, 840, 750.

Mass spectrum (m/e): 406 (M+), 349, 311, 237, 195, 121, 75 (HOMe$_2$Si+).

EXAMPLE 30

Synthesis 10 of a monomer

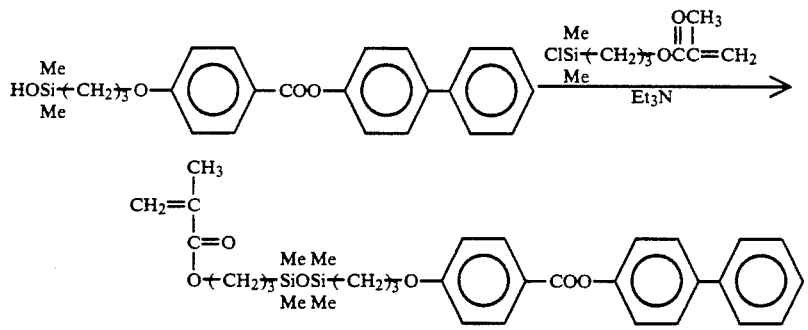

2.00 g (4.92 mmol) of 4-biphenyl p-(3-dimethylhydroxysilylpropoxy)benzoate obtained in Example 29 was dissolved in 20 Ml of tetrahydrofuran under an argon gas atmosphere. To this solution, 1.00 ml (7.17 mmol) of triethylamine and 1.30 g (5.89 mmol) of 3-methacryloxypropyldimethylchlorosilane were added, and the mixture was stirred overnight at room temperature. A white salt formed, was filtered off while washing it with diethyl ether. The solvent was distilled off, and the residue was purified by silica gel column chromatography to obtain 1.44 g of a colorless viscous liquid. With respect to the obtained product, $^1$H-NMR IR and Mass spectrum analyses were conducted to confirm that it was a monomer having the above structure. (yield: 49.5%)

$^1$H-NMR spectrum, δ (CDCl$_3$, ppm): 0.08 (s, 12H, Si—CH$_3$), 0.43-0.76 (m, 4H, Si—CH$_2$CH$_2$CH$_2$—O×2), 1.53-1.96 (m, 4H, Si—CH$_2$CH$_2$CH$_2$—O ×2), 1.92 (dd, 3H, CH$_2$=C(CH$_3$)COO—), 3.99 (t, 2H, Si—CH$_2$CH$_2$CH$_2$—O), 4.09 (t, 2H, Si—CH$_2$CH$_2$CH$_2$—O), 5.51 (m, 1H, CH$_2$=C(CH$_3$)COO—), 6.07 (m, 1H, CH$_2$=C(CH$_3$)COO—), 6.95 (d, 2H, proton peak of a phenylene group), 7.20–7.65 (m, 9H, proton peak of a phenylene group), 8.10 (d, 2H, proton peak of a phenylene group)

IR spectrum (cm⁻¹): 2950, 2870, 1730 (characteristic absorption by a carbonyl group), 1605 (characteristic absorption by a phenylene group), 1510, 1485, 1320, 1290, 1250 (characteristic absorption by a Si—C bond), 1200, 1160, 1065 (characteristic absorption by a siloxane bond), 1000, 840, 790, 755.

Mass spectrum (m/e): 590 (M+), 533, 491, 421, 217, 170, 69 (CH$_2$=C(CH$_3$)COO+), 41 (CH$_2$=C(CH$_3$)+).

EXAMPLE 31

Synthesis 13 of a polymer

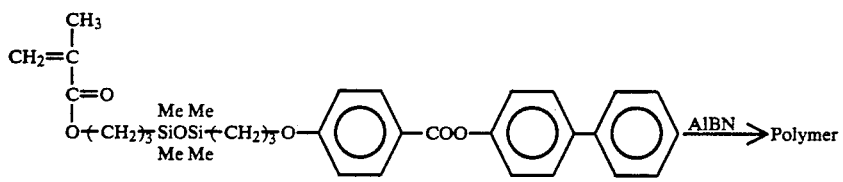

Using 1.20 g (2.00 mmol) of the monomer obtained in Example 30, the polymerization reaction and purification were conducted in the same manner as in Example 3 to obtain 0.68 g a white solid polymer (yield: 57.6%).

With respect to the obtained polymer, ¹H-NMR and IR spectrum analyses and elemental analysis were conducted to confirm that it was a polymer wherein the repeating units were represented by the formula:

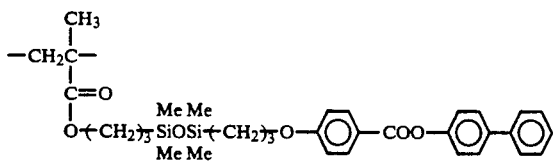

The number average molecular weight and the weight average molecular weight obtained by gel permeation chromatography were 1.41×10⁴ and 2.55×10⁴ respectively, as polystyrene standards. The glass transition temperature of this polymer was 25° C.

¹H-NMR spectrum, δ (CDCl$_3$, ppm): 0.12 (s, 12H, Si—CH$_3$), 0.44–0.70 (m, 4H, Si—C$\underline{H}_2$CH$_2$CH$_2$—O×2), 0.75–1.10 (m, 3H, —CH$_2$C(C$\underline{H}_3$)—), 1.45–2.03 (m, 6H, Si—CH$_2$C$\underline{H}_2$CH$_2$—O×2 and —C$\underline{H}_2$C(CH$_3$)—), 3.89–4.05 (m, 4H, Si—CH$_2$CH$_2$C$\underline{H}_2$—O ×2), 6.95 (d, 2H, proton peak of a phonylene group), 7.19–7.64 (m, 9H, proton peak of a phenylene group), 8.14 (d, 2H, proton peak of a phenylene group), IR spectrum (cm⁻¹): 3020, 2950, 1730 (characteristic absorption by a carbonyl group), 1605 (characteristic absorption by a phenylene group), 1510, 1485, 1250 (characteristic absorption by a Si—C bond), 1200, 1160, 1065 (characteristic absorption by a siloxane bond), 1000, 840, 790, 855, 690.

Elemental analysis (%): Found: C: 66–96, H: 7.39. Calculated: C: 67.08, H: 7.16.

EXAMPLE 32

Synthesis 9 of a silanol compound having a mesogenic group

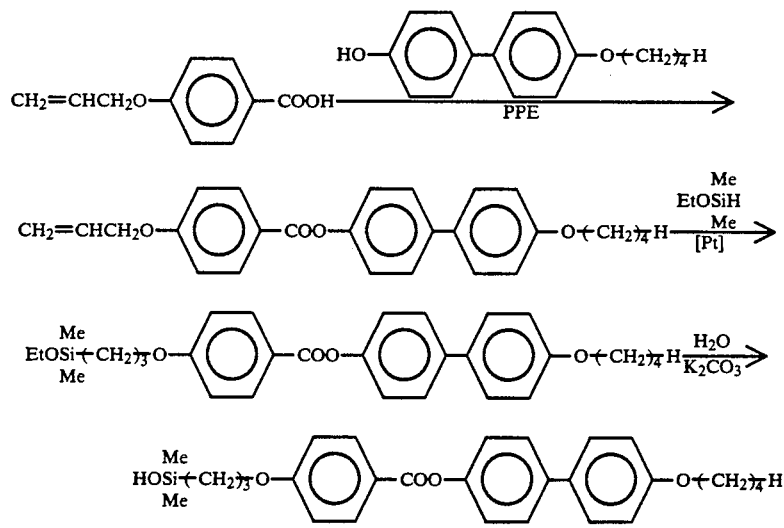

20.0 g of PPE, 4.86 g (27.3 mmol) of p-allyloxybenzoic acid and 6.60 g (27.3 mmol) of 4-butoxy-4'-hydroxybiphenyl were dissolved in 100 ml of chloroform under an argon gas atmosphere, and the solution was stirred overnight at room temperature. Water was added to the solution, and the mixture was extracted with methylene chloride. The organic layer was dried over anhydrous sodium sulfate. The solvent was distilled off, and the residue was purified by silica gel column chromatography to obtain 9.15 g of a white solid. With respect to the obtained product, ¹H-NMR IR and Mass spectrum analyses and elemental analysis were conducted to confirm that it was desired 4-(4'-butoxybiphenyl) p-allyloxybenzoate. (yield: 83.4%).

¹H-NMR spectrum, δ (CDCl$_3$, ppm): 0.98 (t, 3H, —OCH$_2$(CH$_2$)$_2$C$\underline{H}_3$), 1.38–1.89 (m, 4H, —OCH$_2$(C$\underline{H}_2$)$_2$CH$_3$), 4.01 (t, 2H, —OC$\underline{H}_2$(CH$_2$)$_2$CH$_3$, 4.64 (dt, 2H, CH$_2$=CHCH$_2$O—), 5.38 (dd, 1H, CH$_2$=CHCH$_2$O—), 5.55 (dd, 1H, CH$_2$=CHCH$_2$O—), 5.94–6.13 (m, 1H, CH$_2$=CHCH$_2$O—), 6.96 (d, 2H, proton peak of a phenylene group), 7.00 (d, 2H, proton peak of a phenylene group), 7.24 (d, 2H, proton peak of a phenylene group), 7.50 (d, 2H, proton peak of a phenylene group), 7.58 (d, 2H, proton peak of a phenylene group), 8.16 (d, 2H, proton peak of a phenylene group).

IR spectrum (cm$^{-1}$): 2960, 2940, 2880, 1720 (characteristic absorption by a carbonyl group), 1600 (characteristic absorption by a phenylene group), 1510, 1470, 1320, 1245, 1210, 1160, 1070, 1040, 940, 840, 810, 760.

Mass spectrum (m/e): 402 (M+), 161 41 (CH$_2$=CHCH$_2$+).

Elemental analysis (%): Found: C: 77.71, H: 6.39. Calculated: C: 77.59, H: 6.51.

8.75 g (21.0 mmol) of 4-(4'-butoxybiphenyl) p-allyloxybenzoate thus obtained and 7.30 Ml (53.0 mmol) of dimethylethoxysilane were dissolved in 100 Ml of tetrahydrofuran, and 0.50 Ml of a methylene chloride solution of dicyclopentadienylplatinum dichloride (0.1 mol/l) was added thereto. The mixture was stirred at 50° C. for 3 hours under an argon gas atmosphere. The solvent was distilled off to obtain desired 4-(4'-butoxybiphenyl) p-(3-dimethylethoxysilylpropoxy)benzoate as a crude product.

The crude product thereby obtained was dissolved in 35 ml of acetone and 50 ml of tetrahydrofuran. This solution was poured at room temperature into a solution prepared by dissolving 9.0 g (65.1 mmol) of potassium carbonate in 15 ml of water and 45 ml of acetone. To this solution, an aqueous solution prepared by dissolving 9.0 g (65.1 mmol) of potassium carbonate in 45 ml of water, was further added. The mixture was stirred at room temperature for 8 hours. Then, this reaction mixture was poured into an excess amount of ice water containing 30 g of potassium dihydrogen phosphate and extracted with methylene choloride. Then, the organic layer was dried over anhydrous sodium sulfate. The solvent was distilled off, and the residue was purified by silica gel column chromatography to obtain 4.38 g of a white solid. With respect to the obtained product, $^1$H-NMR, IR and Mass spectrum analyses and elemental analysis were conducted to confirm that it was desired 4-(4'-butoxybiphenyl) p-(3-dimethylhydroxysilylpropoxy)benzoate. (yield: 42.2% by two stages).

$^1$H-NMR spectrum, δ (CDCl$_3$, ppm): 0.12 (s, 6H, Si—CH$_3$), 0.52–0.82 (m, 2H, Si—CH$_2$CH$_2$CH$_2$—O), 0.98 (t, 3H, —OCH$_2$(CH$_2$)$_2$CH$_3$), 1.12–1.92 (m, 7H, —OCH$_2$(CH$_2$)$_2$CH$_3$, Si—OH, Si—CH$_2$CH$_2$CH$_2$—O), 3.97 (t, 2H, —OCH$_2$(CH$_2$)$_2$CH$_3$), 4.00 (t, 2H, Si—CH$_2$CH$_2$CH$_2$—O), 6.92 (d, 4H, proton peak of a phenylene group), 7.20 (d, 2H, proton peak of a phenylene group), 7.84 (d, 2H, proton peak of a phenylene group), 7.92 (d, 2H, proton peak of a phenylene group), 8.10 (d, 2H, proton peak of a phenylene group).

IR spectrum (cm$^{-1}$): 3400 (characteristic absorption by a hydroxyl group), 2960, 2940, 2880, 1740 (characteristic absorption by a carbonyl group), 1720, 1620 (characteristic absorption by a phenylene group), 1510, 1490, 1440, 1410, 1260 (characteristic absorption by a Si—C bond), 1220, 1175, 1090, 1060, 1010, 990, 900, 840, 820, 780.

Mass spectrum (m/e): 478 (M+), 416, 362, 242, 186, 121, 75 (HOMe$_2$Si+)

Elemental analysis (%): Found: C: 70.23, H: 7.05. Calculated: C: 70.28, H: 7.16.

EXAMPLE 33

Synthesis ! 1 of a monomer

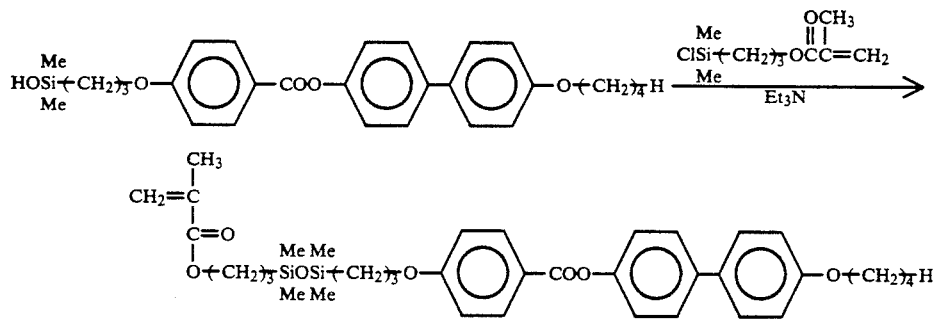

3.90 g (8.15 mmol) of 4-(4'-butoxybiphenyl) p-(3-dimethylhydroxysilylpropoxy)benzoate obtained in Example 32, was dissolved in 30 mg of tetrahydroduran under an argon gas atmosphere. To this solution 3.27 mg (23.7 mmol) of triethylamine and 2.10 g (9.46 mmol) of 3-methacryloxypropyldimethylchlorosilane were added, and the mixture was stirred overnight at room temperature. A white salt formed was filtered off while washing it with diethyl ether. The solvent was distilled off, and the residue was purified by silica gel column chromatography to obtain 3.00 g of a white solid. With respect to the obtained product, $^1$H-NMR IR and Mass spectrum analyses and elemental analysis were conducted to confirm that it was a monomer having the above structure. (yield: 55.5%).

$^1$H-NMR spectrum, δ (CDCl$_3$, ppm): 1.10 (s, 12H, Si—CH$_3$), 0.54–0.86 (m, 4H, Si-CH$_2$CH$_2$CH$_2$—O×2), 1.00 (t, 3H,—OCH$_2$(CH$_2$)$_2$CH$_3$), 1.20–1.90 (m, 4H, Si-—CH$_2$CH$_2$CH$_2$—O ×2, —OCH$_2$(CH$_2$)$_2$CH$_3$), 1.94 (dd, 3H, CH$_2$=C (CH$_3$) COO—), 4.02 (t, 4H, Si-—CH$_2$CH$_2$CH$_2$—O, —OCH$_2$(CH$_2$)$_2$CH$_3$), 4.11 (t, 2H, Si—CH$_2$CH$_2$CH$_2$—O), 5.54 (m, 1H, CH$_2$=C(CH$_3$)COO—), 6.10 (m, 1H, CH$_2$=C(CH$_3$)COO—), 6.97 (d, 4H, proton peak of a phenylene group), 7.27 (d, 2H, proton peak of a phenylene group), 7.51 (d, 2H, proton peak of a phenylene group), 7.58 (d, 2H, proton peak of a phenylene group), 8.16 (d, 2H, proton peak of a phenylene group).

IR spectrum (cm$^{-1}$): 2960, 2940, 2880, 1730 (characteristic absorption by a carbonyl group), 1605 (characteristic absorption by a phenylene group), 1500, 1470, 1320, 1290, 1250 (characteristic absorption by a Si—C bond), 1215, 1170, 1070 (characteristic absorption by a siloxane bond), 1040, 1010, 970, 900, 840, 810.

Mass spectrum (m/e): 662 (M+), 493, 421, 379, 337, 242, 217, 121 69 (CH₂=C(CH₃)COO+), 41 (CH₂=C(CH₃)+).

Elemental analysis ( % ): Found: C: 66.94, H: 7.71. Calculated: C: 67.03, H: 7.60.

EXAMPLE 34

Synthesis 14 of a polymer

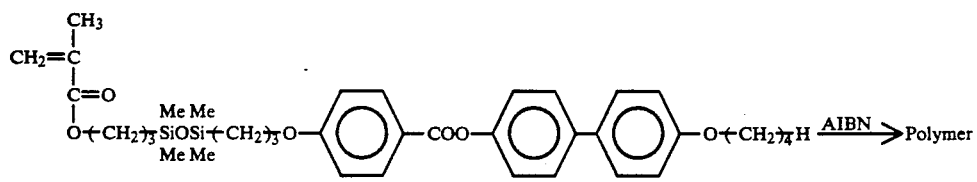

Using 2.00 g (2.86 mmol) of the monomer obtained in Example 33, the polymerization reaction and purification were conducted in the same manner as in Example 3 to obtain 1.40 g of a white solid polymer (yield: 70.0%). With respect to the obtained polymer, ¹H-NMR and IR spectrum analyses and elemental analysis were conducted to confirm that it was a polymer wherein the repeating units were represented by the formula:

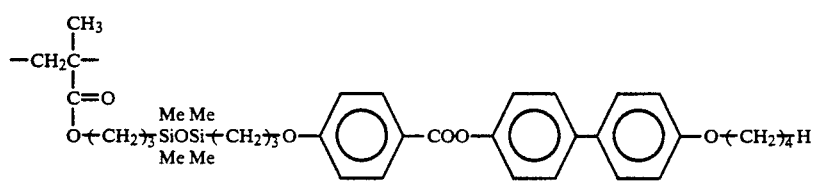

The number average molecular weight and the weight average molecular weight obtained by gel permeation chromatography were 2.12×10⁴ and 4.44×10⁴ respectively, as polystyrene standards. The glass transition temperature of this polymer was 21° C. Further, from the DSC measurements and the polarizing microscopic observation, this polymer was found to show a smectic liquid crystal phase within a wide temperature range of from 55° C. to 156° C. ¹H-NMR spectrum, δ (CDCl₃, ppm): 0.10 (s, 12H, Si—CH₃), 0.54–0.62 (m, 4H, Si—CH₂CH₂CH₂—O×2), 0.88–1.43 (m, 6H, —CH₃C(CH₃)—, —OCH₂(CH₂)₂CH₃), 1.58–1.83 (m, 10H, Si—CH₂CH₂CH₂—O ×2, —CH₂C(CH₃)—, —OCH₂(CH₂)₂CH₃), 3.96 (m, 6H, Si—CH₂CH₂CH₂—O×2, —OCH₂(CH₂)2CH₃), 6.97 (d, 4H, proton peak of a phenylene group), 7.27 (d, 2H, proton peak of a phenylene group), 7.54 (d, 2H, proton peak of a phenylene group), 7.60 (d, 2H, proton peak of a phenylene group), 8.16 (d, 2H, proton peak of a phenylene group).

IR spectrum (cm⁻¹): 2960, 2880, 1730 (characteristic absorption by a carbonyl group), 1605 (characteristic absorption by a phenylene group), 1510, 1500, 1470, 1250 (characteristic absorption by a Si—C bond), 1210, 1165, 1070 (characteristic absorption by a siloxane bond), 1040, 1000, 840, 800, 760

Elemental analysis (%): Found: C: 66.96, H: 7.74. Calculated: C: 67.03, H: 7.60.

EXAMPLE 35

Synthesis 10 of a silanol compound having a mesogenic group

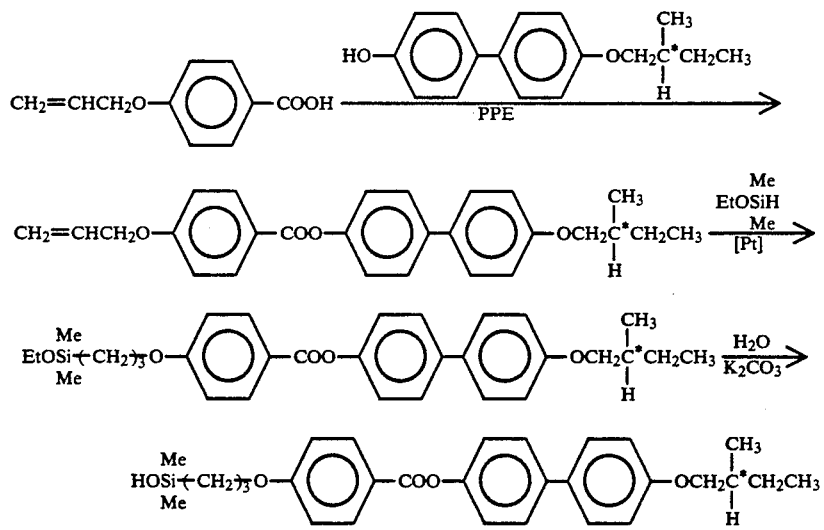

23.4 g of PPE, 3.83 g (21.5 mmol) of p-allyloxybenzoic acid and 5.50 g (21.5 mmol) of 4-(S-2-methylbutoxy)-4'-hydroxybiphenyl, were dissolved in 120 ml of chloroform under an argon atmosphere, and the solution was stirred overnight at room temperature. Water was added to the solution, and the mixture was extracted with methylene chloride. The organic layer was dried over anhydrous sodium sulfate. The solvent was distilled off, and the residue was purified by silica gel column chromatography to obtain 7.28 g of a white solid. With respect to the obtained product, $^1$H-NMR IR and Mass spectrum analyses and elemental analysis were conducted to confirm that it was desired 4-(4'-(S-2-methylbutoxy)biphenyl) p-allyloxybenzoate. (yield: 81.5%).

$^1$H-NMR spectrum, δ (CDCl$_3$, ppm): 0.98 (t, 3H, —OCH$_2$CH(CH$_3$)CH$_2$CH$_3$), 1.04 (d, 3H, —OCH$_2$H(CH$_3$)CH$_2$CH$_3$), 1.09-1.45 (m, 1H, —OCH$_2$CH$_{(CH3)}$CH$_2$CH$_3$), 1.69-1.90 (m, 2H, —OCH$_2$CH(CH$_3$)CH$_2$CH$_3$), 3.83 (dd, 2H, —OCH$_2$CH(CH$_3$)CH$_2$CH$_3$), 4.64 (dr, 2H, CH$_2$=CHCH$_2$O—), 5.37 (dd, 1H, CH$_2$=CHCH$_2$O—), 5.44 (dd, 1H, CH$_2$=CHCH$_2$O—), 5.85-6.25 (m, 1H, CH$_2$=CH$_{CH2}$O—), 6.97 (d, 2H, proton peak of a phenylene group), 7.00 (d, 2H, proton peak of a phenylene group), 7.24 (d, 2H, proton peak of a phenylene group), 7.51 (d, 2H, proton peak of a phenylene group), 7.58 (d, 2H, proton peak of a phenylene group), 8.17 (d, 2H, proton peak of a phenylene group).

IR spectrum (cm$^{-1}$): 3060, 3000, 2970, 1770 (characteristic absorption by a carbonyl group), 1650, 1620 (characteristic absorption by a phenylene group), 1545, 1510, 1490, 1450, 1445, 1420, 1330, 1300, 1265, 1220, 1150, 1125, 1080, 1040, 950, 910, 880, 845, 800, 720, 690.

Mass spectrum (m/e): 416 (M+), 356, 256, 186, 161, 105, 41 (CH$_2$=CHCH$_2$+).

Elemental analysis (%): Found: C: 77.88, H: 6.77 Calculated: C: 77.86, H: 6.78.

7.00 g (16.8 mmol) of 4-(4'-(S-2-methylbutoxy)biphenyl) p-allyloxybenzoate thus obtained and 5.90 ml (44.3 mmol) of dimethylethoxysilane were dissolved in 50 ml of tetrahydrofuran, and 0.50 ml of a methylene chloride solution of dicyclopentadienylplatinum dichloride (0.1 mol/l) was added thereto. The mixture was stirred at 50° C. for 3 hours under an argon gas atmosphere. The solvent was distilled off to obtain desired 4-(4'-(S-2-methylbutoxy)biphenyl) p-(3-dimethylethoxysilylpropoxy)benzoate as a crude product.

The crude product thus obtained was dissolved in 45 ml of acetone and 30 ml of tetrahydrofuran. This solution was poured into a solution prepared by dissolving 9.0 g (65.1 mmol) of potassium carbonate in 15 ml of water and 45 ml of acetone. To this solution, an aqueous solution prepared by dissolving 9.0 g (65.1 mmol) of potassium carbonate in 45 ml of water, was further added. The mixture was stirred at room temperature for 2 hours. Then, this reaction mixture was poured into an excess amount of ice water containing 20 g of potassium dihydrogen phosphate and extracted with methylene chloride. Then, the organic layer was dried over anhydrous sodium sulfate. The solvent was distilled off, and the residue was purified by silica gel column chromatography to obtain 4.13 g of a white solid. With respect to the obtained product, $^1$H-NMR IR and Mass spectrum analyses and elemental analysis were conducted to confirm that it was desired 4-(4'-(S-2-methylbutoxy)biphenyl) p-(3-dimethylhydroxysilylpropoxy)benzoate. (yield: 49.9% by two stages).

$^1$H-NMR spectrum, δ (CDCl$_3$, ppm): 0.10 (s, 6H, Si—CH$_3$), 0.59-0.89 (m, 2H, Si—CH$_2$CH$_2$CH$_2$—O), 0.96 (t, 3H, —OCH$_2$CH(CH$_3$)CH$_2$CH$_3$), 1.04 (d, 3H, —OCH$_2$CH(CH$_3$)CH$_2$CH$_3$), 1.09-1.49 (m, 1H, —OCH$_2$CH$_{(CH3)}$CH$_2$CH$_3$), 1.60-2.19 (s, 5H, Si—OH, Si—CH$_2$CH$_2$CH$_2$—O, —OCH$_2$CH(CH$_3$)CH$_2$CH$_3$), 3.83 (dd, 2H, —OCH$_2$CH(CH$_3$)CH$_2$CH$_3$), 4.05 (t, 2H, Si—CH$_2$CH$_2$CH$_2$—O), 6.97 (d, 4H, proton peak of a phenylene group), 7.24 (d, 2H, proton peak of a phenylene group), 7.51 (d, 2H, proton peak of a phenylene group), 7.58 (d, 2H, proton peak of a phenylene group), 8.16 (d, 2H, proton peak of a phenylene group).

IR spectrum (cm$^{-1}$): 3400 (characteristic absorption by a hydroxyl group), 2960, 2930, 2870, 1730 (characteristic absorption by a carbonyl group), 1700, 1605 (characteristic absorption by a phenylene group), 1495, 1470, 1250 (characteristic absorption by a Si—C bond), 1210, 1165, 1070, 1040, 1005, 990, 840, 800, 760.

Mass spectrum (m/e): 492 (M+), 237, 195, 121, 75 (HOMe$_2$Si+).

Elemental analysis (%): Found: C: 70.61, H: 7.38. Calculated: C: 70.70, H: 7.37.

EXAMPLE 36

Synthesis 12 of a monomer

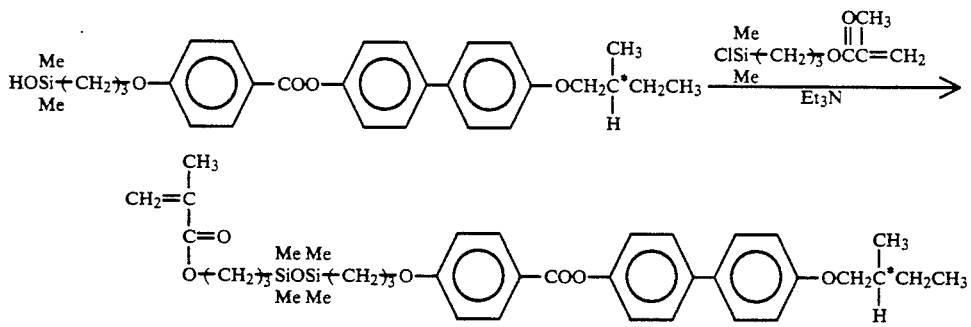

3.90 g (7.92 mmol) of 4-(4'-S-2-methylbutoxy)biphenyl) p-(3-dimethylhydroxysilylpropoxy)benzoate obtained in Example 35 was dissolved in 25 ml of tetrahydrofuran under an argon gas atmosphere. To this solution, 3.28 mg (23.8 mmol) of triethylamine and 2.10 g (9.46 mmol) of 3-methacryloxypropyldimethylchlorosilane were added, and the mixture was stirred overnight at room temperature. A white salt formed was filtered off while washing it with diethyl ether. The solvent was distilled off, and the residue was purified by silica gel column chromatography to obtain 3.81 g of a white solid. With respect to the obtained product $^1$H-NMR IR and Mass spectrum analyses and elemental analysis were conducted to confirm that it was a monomer having the above structure. (yield: 71.1%).

$^1$H-NMR spectrum, δ (CDCl$_3$, ppm): 0.10 (s, 12H, Si—CH$_3$), 0.40-0.80 (m, 4H, Si—CH$_2$CH$_2$CH$_2$—O×2), 0.98 (t, 3H, —OCH$_2$CH(CH$_3$)CH$_2$CH$_3$), 1.04 (t, 3H, —OCH₂CH(CH₃)CH₂CH₃), 1.10–1.49 (m, 1H,—OCH₂CH̲(CH₃)CH₂CH₃), 1.60–1.90 (m, 6H, Si—CH₂CH₂CH₂—O×2, —OCH₂CH(CH₃)CH₂CH₃), 1.97 (dd, 3H, CH₂=C( CH₃)COO—), 3.81 (d, 2H, —OCH₂CH(CH₃) CH₂CH₃), 4.02 (t, 2H, Si—CH₂CH₂CH₂—O), 4.12 (t, 2H, Si—CH₂CH₂CH₂—O), 5.54 (m, 1H, CH₂=C(CH₃)COO—), 6.10 (m, 1H, CH₂=C(CH₃)COO—), 6.97 (d, 4H, proton peak of a phenylene group), 7.24 (d, 2H, proton peak of a phenylene group), 7.51 (d, 2H, proton peak of a phenylene group), 7.58 (d, 2H, proton peak of a phenylene group), 8.16 (d, 2H, proton peak of a phenylene group).

IR spectrum (cm⁻¹): 2990, 2950, 2900, 1730 (characteristic absorption by a carbonyl group), 1640, 1610 (characteristic absorption by a phenylene group), 1585, 1515, 1505, 1470, 1420, 1390, 1320, 1300, 1250 (characteristic absorption by a Si—C bond), 1210, 1170, 1070 (characteristic absorption by a siloxane bond), 1010, 850, 810, 770.

Mass spectrum (m/e): 677 (M+), 507, 421, 379, 337, 256, 217, 121, 69 (CH₂=C(CH₃)COO+), 41 (CH₂=C(CH₃)+).

Elemental analysis (%): Found: C: 67.35, H: 7.86. Calculated: C: 67.42, H: 7.74.

EXAMPLE 37

Synthesis 15 of a polymer

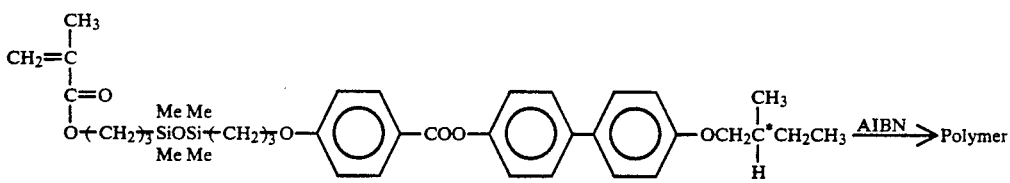

Using 3.60 g (5.32 mmol) of the monomer obtained in Example 36, the polymerization reaction and purification were conducted in the same manner as in Example 3 to obtain 1.96 g of a white solid polymer (yield: 54.5%). With respect to the obtained polymer, ¹H-NMR and IR spectrum analyses and elemental analysis were conducted to confirm that it was a polymer wherein the repeating units were represented by the formula:

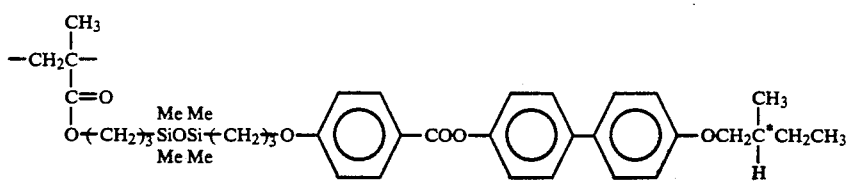

The number average molecular weight and the weight average molecular weight obtained by gel permeation chromatography were a 4.77×10⁴ and 7 96×10⁴, respectively, as polystyrene standards. The glass transition temperature of this polymer was 20° C. Further, from the DES measurement and the polarizing microscopic observation, this polymer was found to show a chiral smectic liquid crystal phase within a wide temperature range of from 45° C. to 127° C.

¹H-NMR spectrum, δ (CDCl₃, ppm): 0.10 (s, 12H, Si—CH₃), 0.40–0.80 (m, 4H, Si—CH̲CH₂CH₂—O×2), 0.95–1.38 (m, 10H, —OCH₂CH̲(CH₃)CH₂CH₃, —OCH₂CH(CH₃)CH₂CH₃, —OCH₂CH(CH₃)CH₂CH₃, —CH₂C(CH₃)—), 1.40–1.90 (m, 8H, Si—CH₂CH₂CH₂—O ×2, —CH₂C(CH₃)—, —OCH₂CH(CH₃)CH̲₂CH₃), 3.80 (d, 2H, —OCH₂CH(CH₃)CH₂CH₃), 4.06 (t, 4H, Si—CH₂CH₂CH̲₂—O ×2), 6.97 (d, 4H, proton peak of a phenylene group), 7.24 (d, 2H, proton peak of a phenylene group), 7.51 (d, 2H, proton peak of a phenylene group), 7.58 (d, 2H, proton peak of a phenylene group), 8.16 (d, 2H, proton peak of a phenylene group).

IR spectrum (cm⁻¹): 2950, 2880, 1730 (characteristic absorption by a carbonyl group), 1610 (characteristic absorption by a phenylene group), 1510, 1500, 1470, 1310, 1250 (characteristic absorption by a Si—C bond), 1210, 1170, 1070 (characteristic absorption by a siloxane bond), 1010, 995, 850, 800.

Elemental analysis (%): Found: C: 67.40, H: 7.86. Calculated: C: .67.42, H: 7.74.

REFERENCE EXAMPLE 38

Synthesis 11 of a silanol compound having a mesogenic group

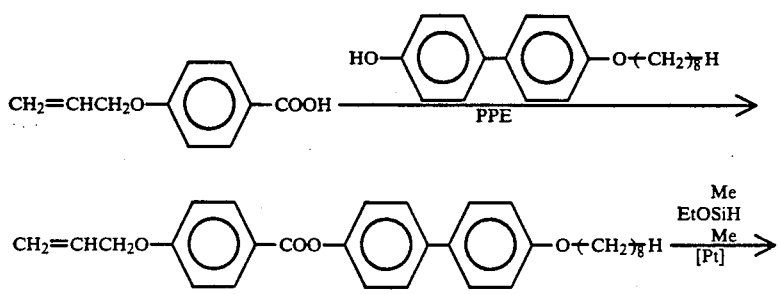

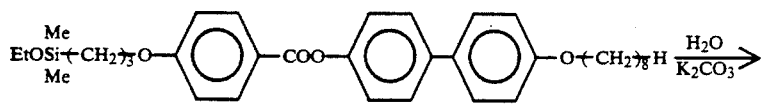

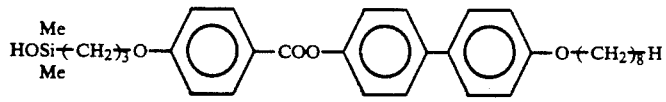

15.0 g of PPE, 2.65 g (15.2 mmol) of p-allyloxybanzoic acid and 4.50 g (13.4 mmol) of octyloxy-4'-hydroxybiphenyl were dissolved in chloroform under an argon gas atmosphere, and the solution was stirred overnight at room temperature. Water was added to the solution, and the mixture was extracted with methylene chloride. The organic layer was dried over anhydrous sodium sulfate. The solvent was distilled off, and the residue was purified by silica gel column chromatography to obtain 5.30 g of a white solid. With respect to the obtained product, $^1$H-NMR IR and Mass spectrum analyses were conducted to confirm that it was desired 4-(4'-octyloxybiphenyl) p-allyloxybenzoate. (yield: 86.2%).

$^1$H-NMR spectrum, δ (CDCl$_3$, ppm): 0.73 (t, 3H, —OCH$_2$(CH$_2$)$_6$CH$_3$), 1.00–1.85 (m, 12H, —OCH$_2$(CH$_2$)$_6$CH$_3$), 3.96 (t, 2H, —OCH$_2$(CH$_2$)$_6$CH$_3$), 4.60 (dt, 2H, CH$_2$=CHCH$_2$O—), 5.36 (dd, 1H, CH$_2$=CHCH$_2$O—), 5.43 (dd, 1H, CH$_2$=CHCH$_2$O—), 5.85–6.23 (m, 1H, CH$_2$=CH$_{CH2}$O—), 6.93 (d, 2H, proton peak of a phenylene group), 6.97 (d, 2H, proton peak of a phenylene group), 7.20 (d, 2H, proton peak of a phenylene group), 7.47 (d, 2H, proton peak of a phenylene group), 7.55 (d, 2H, proton peak of a phenylene group), 8.13 (d, 2H, proton peak of a phenylene group).

IR spectrum (cm$^{-1}$): 2960, 2930, 2850, 1725 (characteristic absorption by a carbonyl group), 1610 (characteristic absorption by a phenylene group), 1500, 1470, 1310, 1290, 1250, 1215, 1165, 1080, 1010, 995, 930, 880, 840, 800, 760, 690.

Mass spectrum (m/e): 458 (M$^+$), 298, 161, 41 (CH$_2$=CHCH$_2^+$). 5.00 g (10.9 mmol) of 4-(4'-octyloxybiphenyl) p-allyloxybenzoate thereby obtained and 2.5 ml (18.2 mmol) of dimethylethoxysilane were dissolved in 50 ml of tetrahydrofuran, and 0.20 ml of a methylene chloride solution of dicyclopentadienylplatinum dichloride (0.1 mol/l) was added thereto. The mixture was stirred at 50° C. for 3 hours under an argon gas atmosphere. The solvent was distilled off to obtain desired 4-(4'-octyloxybiphenyl) p-(3-dimethylethoxysilylpropoxy)benzoate as a crude product.

The crude product thereby obtained was dissolved in 40 ml of acetone and 60 ml of tetrahydrofuran. This solution was poured at room temperature into a solution prepared by dissolving 3.5 g (25.3 mmol) of potassium carbonate in 50 ml of water and 120 ml of tetrahydrofuran. To this solution, an aqueous solution prepared by dissolving 3.5 g (25.3 mmol) of potassium carbonate in 100 ml of water, was further added. The mixture was stirred at room temperature for 2 hours. Then, this reaction mixture was poured into an excess amount of ice water containing 12 g of potassium dihydrogen phosphate and extracted with methylene chloride. Then, the organic layer was dried over anhydrous sodium sulfate. The solvent was distilled off, and the residue was purified by silica gel column chromatography to obtain 4.01 g of a white solid. With respect to the obtained product, $^1$H-NMR IR and Mass spectrum analyses were conducted to confirm that it was desired 4-(4'-ocryloxybiphenyl) p-(3-dimethylhydroxysilylpropoxy)benzoate. (yield: 68.8% by two stages).

$^1$H-NMR spectrum, δ (CDCl$_3$, ppm): 0.20 (s, 6H, Si—CH$_3$), 0.58–0.70 (m, 2H, Si—CH$_2$CH$_2$CH$_2$—O), 0.75 (t, 3H, —OCH$_2$(CH$_2$)$_6$CH$_3$), 1.20–2.10 (m, 15H, Si—OH, Si—CH$_2$CH$_2$CH$_2$—O, —OCH$_2$(CH$_2$)$_6$CH$_3$), 4.01 (t, 2H, —OC$_2$(CH$_2$)$_6$CH$_3$), 4.06 (t, 2H, Si—CH$_2$CH$_2$CH$_2$—O), 6.98 (d, 4H, proton peak of a phenylene group), 7.25 (d, 2H, proton peak of a phenylene group), 7.52 (d, 2H, proton peak of a phenylene group), 7.59 (d, 2H, proton peak of a phenylene group), 8.17 (d, 2H, proton peak of a phenylene group).

IR spectrum (cm$^{-1}$): 3280 (characteristic absorption by a hydroxyl group), 2960, 2940, 2860, 1740 (characteristic absorption by a carbonyl group), 1610 (characteristic absorption by a phenylene group), 1510, 1500, 1470, 1400, 1250 (characteristic absorption by a Si—C bond), 1220, 1160, 1075, 1040, 1000, 890, 860, 840, 800, 760, 680.

Mass spectrum (m/e): 534 (M$^+$), 418, 298, 237, 195, 121, 75 (HOMe$_2$Si$^+$).

EXAMPLE 39

Synthesis 13 of a monomer

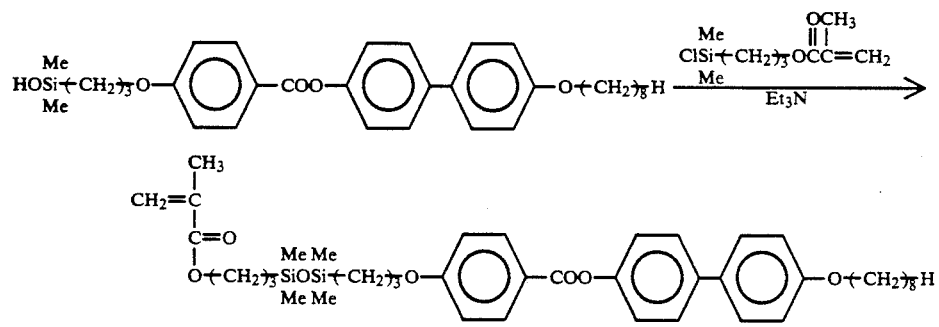

3.60 g (6.73 mmol) of 4-(4'-octyloxybiphenyl) p-(3-dimethylhydroxysilylpropoxy)benzoate obtained in Example 38 was dissolved in 25 ml of tetrahydrofuran under an argon gas atmosphere. To this solution, 2.00 ml (14.3 mmol) of triethylamine and 1.48 g (6.71 mmol) of 3-aethacryloxypropyldimethylchlorosilane were added, and the mixture was stirred overnight at room temperature. A white salt formed was filtered off by washing it with diethyl ether. The solvent was distilled off, and the residue was purified by silica gel column chromatography to obtain 2.01 g of a white solid. With respect to the obtained product, $^1$H-NMR IR and Mass spectrum analyses were conducted to confirm that it was a monomer having the above structure. (yield: 38.2%).

$^1$H-NMR spectrum, δ (CDCl$_3$, ppm): 0.11 (s, 12H, Si—CH$_3$), 0.32–0.65 (m, 4H, Si—CH$_2$CH$_2$CH$_2$—O×2), 0.75 (t, 3H,—OCH$_2$(CH$_2$)$_6$CH$_3$), 1.10–1.90 (m, 16H, Si—CH$_2$CH$_2$CH$_2$—O ×2, —OCH$_2$(CH$_2$)$_6$CH$_3$), 1.95 (s, 3H, CH$_2$=C(CH$_3$)COO—), 4.02 (t, 2H, —OCH$_2$(CH$_2$)$_6$CH$_3$), 4.07 (t, 2H, Si—CH$_2$CH$_2$CH$_2$—O), 4.12 (t, 2H, Si—CH$_2$CH$_2$CH$_2$—O), 5.54 (m, 1H, CH$_2$=C(CH$_3$)COO—), 6.11 (m, 1H, CH$_2$=C(CH$_3$)COO—), 6.97 (d, 4H, proton peak of a phenylene group), 7.24 (d, 2H, proton peak of a phenylene group), 7.51 (d, 2H, proton peak of a phenylene group), 7.59 (d, 2H, proton peak of a phenylene group), 8.16 (d, 2H, proton peak of a phenylene group).

IR spectrum (cm$^{-1}$): 3000, 2950, 2900, 1730 (characteristic absorption by a carbonyl group), 1610 (characteristic absorption by a phonylone group), 1510, 1500, 1260 (characteristic absorption by a Si—C bond), 1210, 1170, 1070 (characteristic absorption by a siloxane bond), 900, 840, 820, 770.

Mass spectrum (m/e): 719 (M+), 549, 421, 379, 298, 217, 121, 69 (CH$_2$=C(CH$_3$)COO+), 41 ( CH$_2$=C(CH$_3$)+).

EXAMPLE 40

Synthesis 16 of a polymer

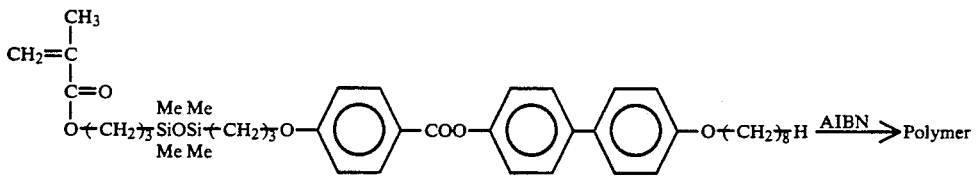

Using 1.20 g (1.67 mmol) of the monomer obtained in Example 39, the polymerization reaction and purification were conducted in the same manner as in Example 3 to obtain 0.78 g of a white solid polymer (yield: 65.0%). With respect to the obtained polymer, $^1$H-NMR and IR spectrum analyses and elemental analysis were conducted to confirm that it was a polymer wherein the repeating units were represented by the formula:

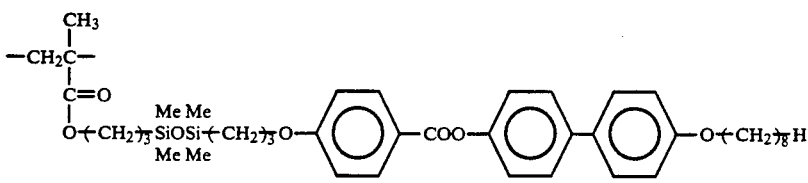

The number average molecular weight and the weight average molecular weight obtained by gel permeation chromatography, were 2.37×10$^4$ and 4.38×10$^4$ respectively, as polystyrene standards. The glass transition temperature of this polymer was 19° C. Further, from the DES measurement and the polarizing microscopic observation, this polymer was found to show a smectic liquid crystal phase within a wide temperature range of from 45° C. to 164° C.

$^1$H-NMR spectrum, δ (CDCl$_3$, ppm): 0.10 (s, 12H, Si—CH$_3$), 0.33–0.70 (m, 4H, Si—CH$_2$CH$_2$CH$_2$—O×2), 0.72–1.35 (m, 6H, —CH$_2$C(CH$_3$)—, —OCH$_2$(CH$_2$)$_6$CH$_3$), 1.45–1.98 (m, 18H, Si—CH$_2$CH$_2$CH$_2$—O ×2, —CH$_2$C(CH$_3$)—, —OCH$_2$(CH$_2$)$_6$CH$_3$), 3.94 (m, 6H, Si—CH$_2$CH$_2$CH$_2$—O×2, —OCH$_2$(CH$_2$)$_6$CH$_3$), 6.91 (d, proton peak of a phenylene group), 7.20 (d, 2H, proton peak of a phenylene group), 7.48 (d, 2H, proton peak of a phenylene group), 7.59 (d, 2H, proton peak of a phenylene group), 8.13 (d, 2H, proton peak of a phenylene group).

IR spectrum (cm$^{-1}$): 2970, 2950, 2890, 1735 (characteristic absorption by a carbonyl group), 1610 (characteristic absorption by a phenylene group), 1510, 1500, 1480, 1255 (characteristic absorption by a Si—C bond), 1210, 1165, 1060 (characteristic absorption by a siloxane bond), 910, 840, 800, 760.

Elemental analysis (%): Found: C: 68.33, H: 8.28. Calculated: C: 68.39, H: 8.26.

We claim:

1. A silanol compound having a mesogenic group, of the following formula (III):

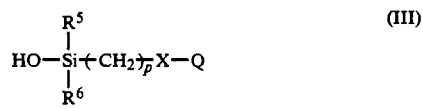

wherein each of R$^5$ and R$^6$ which may be the same or different, is an alkyl group or a phenyl group, X is a single bond, an oxygen atom, or a group of the formula —COO— or —OCO—, Q is a mesogenic group, and p is an integer of from 2 to 20.

2. The silanol compound according to claim 1, wherein the mesogenic group Q is selected from the group consisting of biphenyl, biphenyl ether, phenyl benzoate, biphenyl benzoate, benzylidene aniline, stilbene, azoxybenzene, azobenzene, a schiff base, cyclohexylphenyl ether, cyclohexylbenzene, phenyl cyclohexylcarboxylate, biphenyl cyclohexylcarboxylate, cholesterol, cholestane and derivatives thereof.

3. The silanol compound according to claim 1, wherein the alkyl group for each of $R^5$ and $R^6$ is a methyl group, an ethyl group, a propyl group, an isopropyl group, a butyl group, an iso-butyl group, a t-butyl group, a pentyl group or a hexyl group.

4. The silanol compound according to claim 1, wherein each of $R^5$ and $R^6$ is a methyl group, and p is an integer of from 3 to 10.

5. A process for producing silanol compound having a mesogenic group, of the following formula (III):

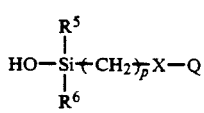
(III)

wherein each of $R^5$ and $R^6$ which may be the same or different, is an alkyl group or a phenyl group, X is a single bond, an oxygen atom, or a group of the formula —COO— or —OCO—, Q is a mesogenic group, and p is an integer of from 2 to 20, which comprises reacting an alkenyl compound having a mesogenic group, of the following formula (VI):

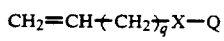
(VI)

wherein X and Q are as defined above, and q is an integer of from 0 to 18, and a compound of the following formula (VII):

(VII)

wherein $R^5$ and $R^6$ are as defined above, and R' is an alkyl group, in the presence of a hydrosilylation catalyst, by mixing them so that the compound of the above formula (VII) would be at least equimolar to the compound of the above formula (VI), to obtain a compound of the following formula (VIII):

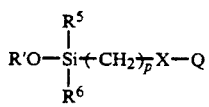
(VIII)

wherein $R^5$, $R^6$, R', Q and p are as defined above, and hydrolyzing the compound of the above formula (VIII) to obtain the compound of the above formula (III).

6. The silanol compound according to claim 1, wherein the mesogenic group Q is a biphenyl benzoate.

7. The silanol compound according to claim 6, 4-(4'-cyanobiphenyl)p-(3-dimethylhydroxysilylpropoxy)benzoate.

* * * * *